(12) United States Patent
Nishii et al.

(10) Patent No.: US 9,538,969 B2
(45) Date of Patent: Jan. 10, 2017

(54) MANAGEMENT APPARATUS

(71) Applicant: CANON KABUSHIKI KAISHA, Tokyo (JP)

(72) Inventors: Yuichi Nishii, Kawasaki (JP); Hikaru Tanaka, Tokyo (JP); Tomohiko Haraguchi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/801,475

(22) Filed: Jul. 16, 2015

(65) Prior Publication Data

US 2016/0029986 A1 Feb. 4, 2016

(30) Foreign Application Priority Data

Aug. 1, 2014 (JP) .................................. 2014-158124

(51) Int. Cl.
*A61B 6/00* (2006.01)

(52) U.S. Cl.
CPC .............. *A61B 6/4233* (2013.01); *A61B 6/465* (2013.01); *A61B 6/542* (2013.01)

(58) Field of Classification Search
CPC ........ A61B 6/4233; A61B 6/465; A61B 6/542
See application file for complete search history.

(56) References Cited

U.S. PATENT DOCUMENTS

| | | | |
|---|---|---|---|
| 8,724,772 B2 | 5/2014 | Nishii | .............................. 378/42 |
| 9,031,194 B2 | 5/2015 | Nishii | ..................... A61B 6/465 |
| 2011/0052016 A1 | 3/2011 | Nishii | ............................ 382/128 |
| 2012/0132810 A1* | 5/2012 | Uchiyama | ................ H04N 5/32 |
| | | | 250/358.1 |
| 2012/0243663 A1 | 9/2012 | Nishii | ............................ 378/98 |
| 2013/0114793 A1* | 5/2013 | Ohta | .................... A61B 5/0059 |
| | | | 378/63 |
| 2014/0252205 A1 | 9/2014 | Tanaka | ........................ 250/208.1 |
| 2014/0258907 A1 | 9/2014 | Tanaka | ........................... 715/771 |

FOREIGN PATENT DOCUMENTS

| | | |
|---|---|---|
| JP | 11-155847 A | 6/1999 |
| JP | 4684747 B | 5/2011 |

* cited by examiner

*Primary Examiner* — Mark R Gaworecki
(74) *Attorney, Agent, or Firm* — Fitzpatrick, Cella, Harper & Scinto

(57) ABSTRACT

A management apparatus which manages an image captured in a radiation detection apparatus by irradiation with radiation, manages imaging information which is input by a user and serves as information for imaging, obtains the captured image, and associates the obtained image with the imaging information. The management apparatus, when a mis-exposure notification is received from the radiation detection apparatus and manages the necessary imaging information, obtains the captured image.

24 Claims, 22 Drawing Sheets

MANAGEMENT APPARATUS

BACKGROUND OF THE INVENTION

1. Field of the Invention

The present invention relates to a radiation detection technique and, more particularly, to a management apparatus and management method for managing a radiation detection apparatus capable of capturing a radiation image without exchanging synchronization signals with a radiation generating apparatus, and a non-transitory computer-readable storage medium.

2. Description of the Related Art

Recently, the digitization of radiation images has been promoted in a medical field, leading to many merits. For example, it is possible to speed up diagnosis by allowing a user to quickly check captured images on a display device or the like upon digital transmission to it. In addition, digitization improves diagnosis accuracy with respect to a fine lesion as well as automating diagnosis by various types of image processing. Furthermore, since there is no need to secure a film storage space, the space efficiency inside a hospital greatly improves. Moreover, since digital transmission hardly suffers data deterioration, it is possible to transmit captured images to a remote place without any deterioration. By making the most of these features, diagnosis can be received from a highly trained doctor by transmitting images captured in a home care site, a disaster site, or the like to a fully equipped urban hospital.

Radiation detection apparatuses have been commercially available and rapidly popular, which use a digital radiation imaging method of forming an image by converting radiation into an electric signal by using a plurality of radiation detection elements arrayed in a two-dimensional matrix instead of a film. As a radiation detection apparatus of this type, a radiation detection apparatus using an FPD (Flat Panel Detector) has been proposed. In such a radiation detection apparatus, minute radiation detectors, each obtained by stacking a solid-state photoelectric conversion element and a scintillator for converting radiation into visible light, are arranged as image sensing elements in a two-dimensional matrix. Each image sensing element converts irradiated radiation into an electric signal (charge amount) corresponding to the irradiation dose. In general, an FPD can accumulate charges generated by irradiation with radiation in solid-state photoelectric conversion elements by controlling a voltage to be applied to the elements. Then, the FPD reads out charges from the solid-state photoelectric conversion elements by controlling the voltage to be applied to the elements to be another voltage, and forms image data in accordance with the accumulated charge amounts.

When capturing a radiation image by using the FPD, the timing of irradiation with radiation and the timing to perform accumulation (imaging) of charges in the radiation detection apparatus need to be accurately synchronized with each other in consideration of the characteristics of solid-state photoelectric conversion elements in use. For this purpose, there is proposed a radiation imaging system which synchronizes the radiation irradiation timing and the imaging timing by exchanging synchronization signals between the radiation generating apparatus and the FPD, as disclosed in, for example, Japanese Patent No. 4684747. More specifically, the FPD makes preparation for imaging in response to an irradiation request signal from the radiation generating apparatus. Then, an irradiation permission signal is transmitted to the radiation generating apparatus in accordance with the start of imaging by the FPD (the start of accumulating charges), thereby performing irradiation with radiation. In a radiation imaging system proposed in Japanese Patent Laid-Open No. 11-155847, the FPD detects the radiation irradiation timing by detecting a change of a current caused inside upon irradiation with radiation. The FPD starts imaging in response to the detection as a trigger, thereby establishing synchronization between the radiation irradiation timing and the imaging timing.

In a system in which the radiation generating apparatus and the FPD exchange synchronization signals, as disclosed in Japanese Patent No. 4684747, the radiation generating apparatus and the FPD need to be connected in electrically one-to-one correspondence. This puts a constraint on system building such that the radiation generating apparatus and the FPD require connection interfaces. Further, in a system as disclosed in Japanese Patent No. 4684747, a conventional radiation generating apparatus not coping with the FPD does not have a connection interface and suffers problems such as incapability of imaging by the FPD.

In the radiation imaging system described in Japanese Patent Laid-Open No. 11-155847, the radiation detection apparatus itself detects irradiation with radiation and performs imaging. This system can therefore solve problems arising from the necessity of an electric connection with the radiation generating apparatus. Since no additional apparatus or the like need be connected, the system is satisfactorily flexible. However, the following problems may arise.

In a radiation imaging system in which a radiation generating apparatus and a radiation detection apparatus are not synchronized with each other, the radiation generating apparatus can generate radiation regardless of the state of the radiation detection apparatus and the state of an imaging control apparatus which controls the radiation detection apparatus and displays and saves an image. When irradiation with radiation is performed in a state in which the radiation detection apparatus is not ready yet, a case (first case) is conceivable, in which an obtained image becomes a poor image under the influence of charges remaining in the radiation detection apparatus or the like, and no effective image can be obtained. Also, when irradiation with radiation is performed in a state in which the imaging control apparatus is not ready yet, a case (second case) is also conceivable, in which even if the radiation detection apparatus obtains an effective image, the imaging control apparatus is not ready for controlling the radiation detection apparatus and the image can be neither displayed nor saved. Further, when irradiation with radiation is performed in a state in which the imaging control apparatus has not prepared patient information and examination information, a case (third case) is also conceivable, in which even if the radiation control apparatus obtains an image from the radiation detection apparatus, it cannot appropriately associate the image with patient information and examination information. Re-imaging is necessary in all these cases, causing a problem because ineffective exposure to a patent may be performed.

There is a need for an imaging system in which when the state is improper, as described above, and imaging is performed in spite of mis-exposure, the user is quickly notified of the mis-exposure to stop irradiation by the radiation generating apparatus and make a notification to request re-imaging or the like.

SUMMARY OF THE INVENTION

The present invention has been made to solve the above problems, and provides suppressing the necessity of re-imaging when irradiation with radiation is performed in a state in which a radiation detection apparatus is not ready yet.

According to one aspect of the present invention, there is provided a management apparatus which manages an image captured in a radiation detection apparatus by irradiation with radiation, the management apparatus comprises a management unit configured to manage imaging information which is input by a user and serves as information for imaging, an obtaining unit configured to obtain the captured image, and an association unit configured to associate the obtained image with the imaging information, wherein when a mis-exposure notification is received from the radiation detection apparatus and the management unit manages the necessary imaging information, the obtaining unit obtains the captured image.

Further features of the present invention will become apparent from the following description of exemplary embodiments (with reference to the attached drawings).

DESCRIPTION OF THE EMBODIMENTS

Embodiments of the present invention will now be described with reference to the accompanying drawings. Note that radiation imaging in the following embodiments may be imaging using α-rays, β-rays, γ-rays, or other electromagnetic waves, in addition to imaging using X-rays.

First Embodiment

Figure 1:
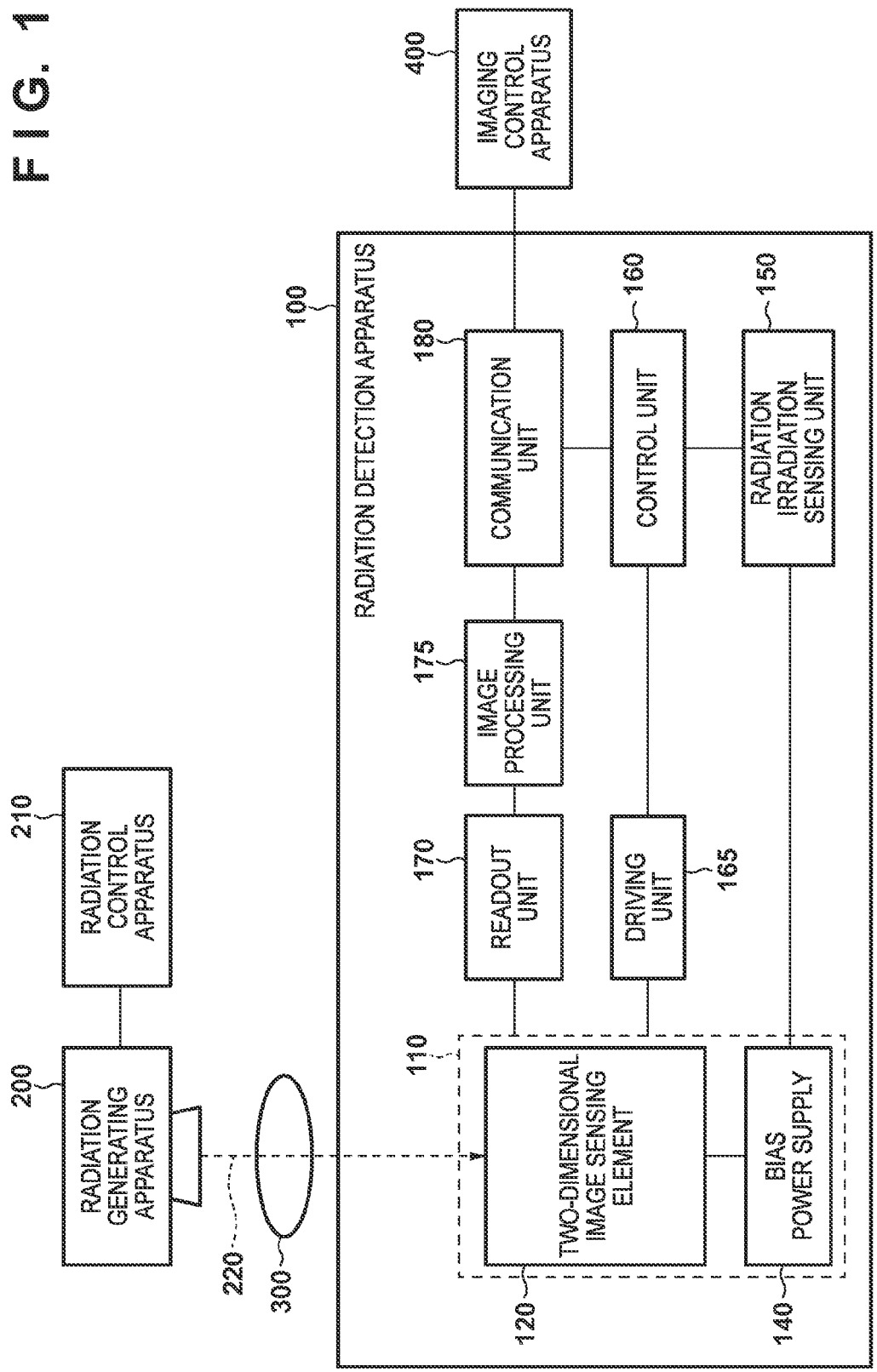
FIG. 1 is a block diagram showing the arrangement of an imaging system according to the first embodiment.

FIG. 1 is a block diagram showing the arrangement of a radiation imaging system (to be referred to as an imaging system hereinafter) 10 according to the first embodiment. Note that radiation imaging may be imaging using α-rays, β-rays, γ-rays, or other electromagnetic waves, in addition to imaging using X-rays. The imaging system according to this embodiment includes a radiation detection apparatus 100, a radiation generating apparatus 200, a radiation control apparatus 210, and an imaging control apparatus 400. The radiation detection apparatus 100 according to this embodiment includes a radiation detector 110 constituted by a two-dimensional image sensing element 120 and a bias power supply 140, a radiation irradiation sensing unit 150, a control unit 160, a driving unit 165, a readout unit 170, an image processing unit 175, and a communication unit 180.

In the radiation detection apparatus 100, the two-dimensional image sensing element 120 is constituted by arraying a plurality of solid-state photoelectric conversion elements in a two-dimensional matrix. The bias power supply 140 supplies a bias voltage to the two-dimensional image sensing element 120. The radiation irradiation sensing unit 150 is connected to the bias power supply 140 and senses irradiation with radiation. The control unit 160 controls various operations of the radiation detection apparatus 100. The readout unit 170 reads out image data. The image processing unit 175 performs image processing on an image read out by the readout unit 170. The communication unit 180 can perform communication by at least either wireless communication or wired communication. Although a general PC (Personal Computer) is assumed as the imaging control apparatus 400, the imaging control apparatus 400 may be a smart device or a mobile phone, and in some cases, an in-hospital server or a cloud system. In some cases, the system may be constituted by incorporating the display-equipped radiation detection apparatus 100 in the imaging control apparatus 400.

The radiation generating apparatus 200 generates pulse-like radiation 220. The radiation control apparatus 210 controls radiation generation conditions such as ON/OFF of radiation, a tube current, and a tube voltage in the radiation generating apparatus 200. The radiation 220 generated by the radiation generating apparatus 200 irradiates an object 300. The radiation 220 having passed through the object 300 enters the two-dimensional image sensing element 120 arranged in the radiation detection apparatus 100. The two-dimensional image sensing element 120 converts the radiation 220 into a radiation image. The converted radiation image is read out via the readout unit 170 and then transferred as digital image data to the imaging control apparatus 400 via the communication unit 180. The imaging control apparatus 400 displays and saves the received image data, and transfers it to a printer or PACS (Picture Archiving and Communication System) (neither is shown).

Figure 2:
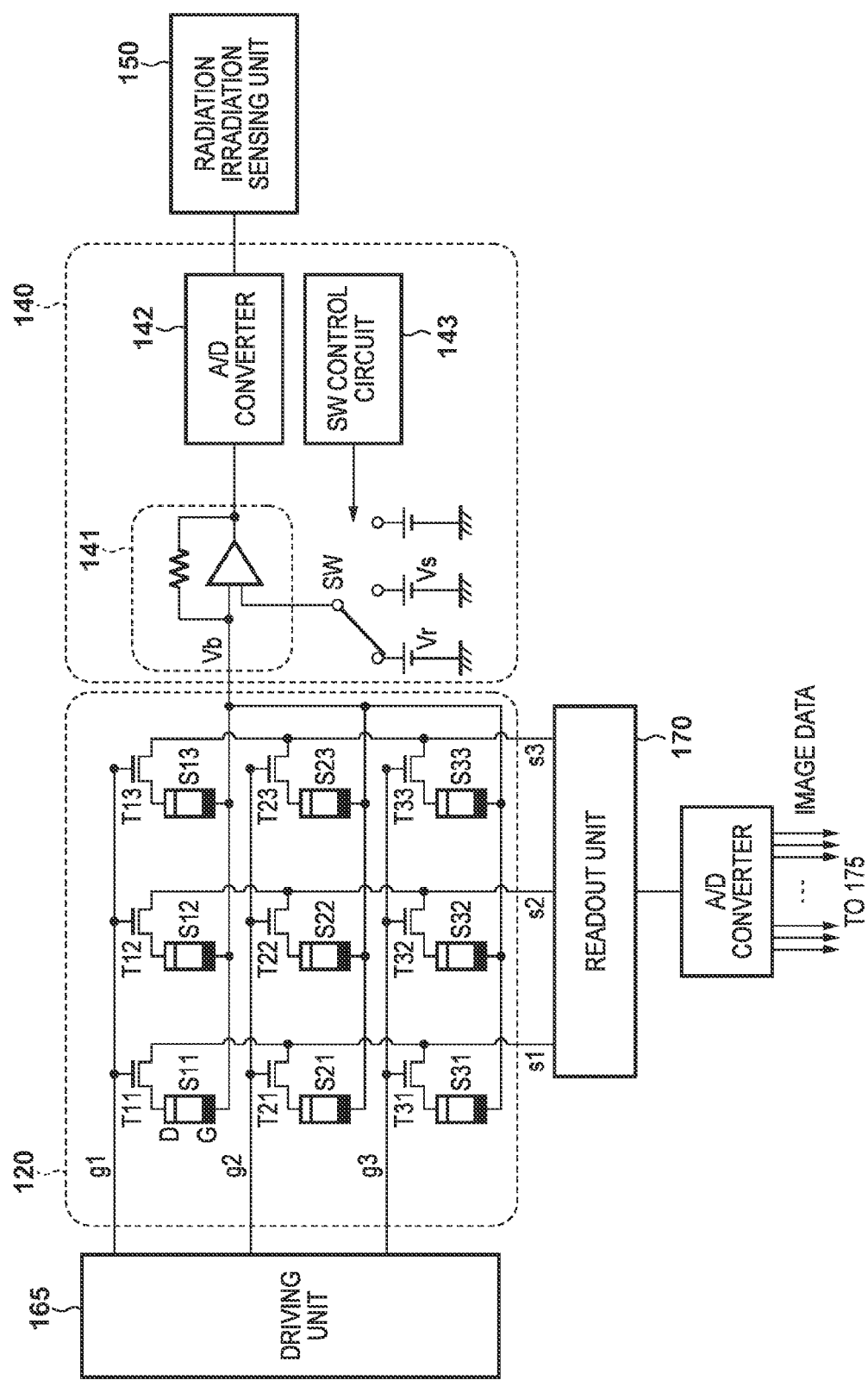
FIG. 2 is a circuit diagram showing the equivalent circuit of a radiation detector according to the first embodiment.

FIG. 2 is a circuit diagram showing the equivalent circuit of the radiation detector 110. The two-dimensional image sensing element 120 is constituted by a plurality of pixels arrayed in an m (row)×n (column) matrix. For the sake of descriptive simplicity, FIG. 2 shows a 3×3 matrix, with m=3 and n=3. However, an actual detection apparatus includes pixels as many as, for example, m=2800 and n=2800. Each pixel is constituted by one of photoelectric conversion elements S11 to S33, a phosphor (not shown) which converts the radiation 220 into light in a wavelength band that can be sensed by the photoelectric conversion element S11, and one of switching elements T11 to T33.

Each of the photoelectric conversion elements S11 to S33 generates and accumulates charges corresponding to the amount of incident radiation. The transmission amount of radiation passing through the object 300 has a different distribution depending on a structure such as a bone or internal organ, a focus of disease, or the like in the object. The photoelectric conversion elements S11 to S33 convert such a different distribution into a charge distribution and accumulate it. As the photoelectric conversion elements S11 to S33, various elements using amorphous silicon and polysilicon are known, as well as a CCD. In this embodiment, MIS photodiodes which are mainly made of amorphous silicon and arranged on an insulating substrate such as a glass substrate are used as the photoelectric conversion elements S11 to S33. However, PIN photodiodes may be used. In addition, a direct type conversion element which directly converts radiation into charges can be used. As the switching elements T11 to T33, transistors each having a control terminal and two main terminals are suitably used. This embodiment adopts thin-film transistors (TFTs).

In FIG. 2, the electrode on the lower electrode side is indicated as a G electrode, and the electrode on the upper electrode side is indicated as a D electrode. The D electrode is electrically connected to one of the two main terminals of the switching element. On the other hand, the G electrode is connected to the bias power supply 140 via a common bias wiring. When taking the first row as an example, the control terminals of the plurality of switching elements T11, T12, and T13 in the row direction are commonly connected to a driving wiring g1 on the first row, and the driving unit 165 supplies a driving signal for controlling the conductive states of the switching elements T11, T12, and T13 via the driving wiring g1 for each row.

When taking the first column as an example, the main terminals of the plurality of switching elements T11, T21, and T31 in the column direction, which are not connected to the photoelectric conversion elements S11, S21, and S31, are electrically connected to a signal wiring s1 on the first column. While the switching elements T11, T21, and T31 are in the conductive state, electric signals corresponding to amounts of charges accumulated in the photoelectric conversion elements S11, S21, and S31 are output to the readout unit 170 via the signal wiring s1. A plurality of signal wirings s1 to s3 in the column direction in parallel transmit electric signals read out from a plurality of pixels to the readout unit 170.

The readout unit 170 includes a multiplexer (not shown) which sequentially processes readout electric signals in parallel and outputs the resultant signals as serial image signals, and a buffer amplifier (not shown) which outputs the image signals after impedance conversion. An A/D converter 142 converts the image signal serving as the analog electric signal output from the buffer amplifier into digital image data. This image data is transmitted to the imaging control apparatus 400 via the image processing unit 175 and the communication unit 180.

The bias power supply 140 supplies a bias voltage Vb to the G electrodes of the photoelectric conversion elements S11 to S33 via the bias wirings, and also outputs current information including a change of the amount of current supplied to the bias wirings. In this embodiment, a circuit which outputs the current information includes a current-voltage conversion circuit 141 constituted by an operational amplifier and a resistor, and the A/D converter 142 which converts a converted output voltage into a digital value. However, this is not exhaustive. For example, a current-voltage conversion circuit using a shunt resistor may be used. In addition, the bias power supply 140 may directly output the output voltage of the current-voltage conversion circuit 141. Furthermore, the bias power supply 140 may output a physical amount corresponding to the amount of current supplied to the bias wiring. The digital current information is sent to the radiation irradiation sensing unit 150. Irradiation with radiation can be sensed by capturing a change of the current amount caused during radiation irradiation. Note that an SW control circuit 143 controls a voltage to be applied to the G electrode. The SW control circuit 143 performs control to apply a voltage Vr during the refresh period of the photoelectric conversion element (period of a refresh mode) and a voltage Vs during the remaining period (period of a photoelectric conversion mode).

Figure 3:
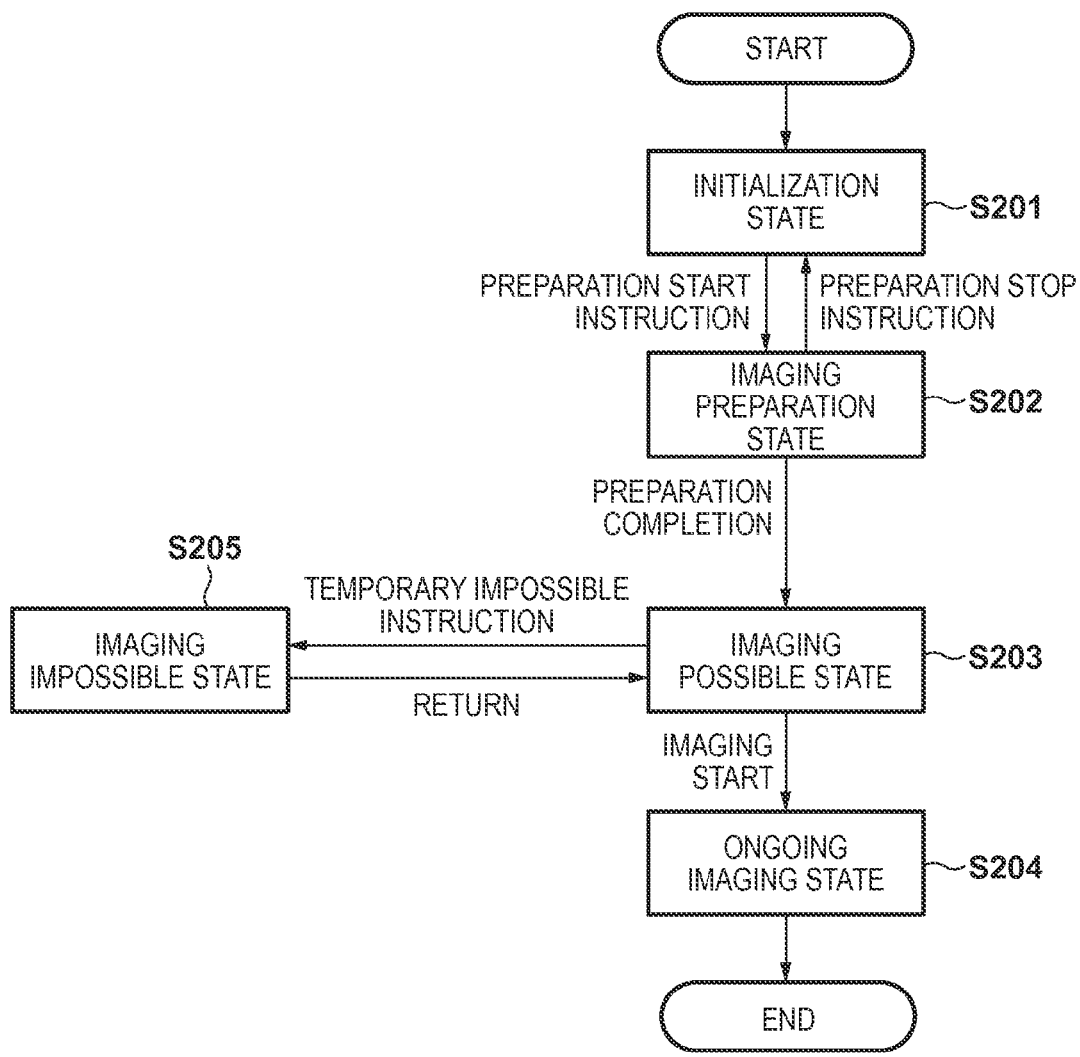
FIG. 3 is a flowchart showing an example of the state transition of a radiation detection apparatus according to the first embodiment.

FIG. 3 is a flowchart showing an example of the state transition of the radiation detection apparatus 100 according to the first embodiment. The control state of the radiation detection apparatus 100 mainly takes five states: an initialization state, imaging preparation state, imaging possible state, ongoing imaging state, and imaging impossible state.

Step S201 represents that the radiation detection apparatus 100 is in the initialization state. The initialization state is a state in which the photoelectric conversion elements on the two-dimensional image sensing element 120 in the radiation detection apparatus 100 are initialized. That is, the initialization state is a state in which application of a voltage to the electrodes of the photoelectric conversion elements is stopped. The initialization state is the same state as a so-called sleep state in a general PC (that is, a power-saving standby power supply mode in which power can be greatly saved in comparison with a normal activation state, and a quick return is possible because information is kept held in the memory). The imaging control apparatus 400 notifies the radiation detection apparatus 100 of a preparation start instruction, and the radiation detection apparatus 100 transits to step S202.

Step S202 represents that the radiation detection apparatus 100 is in the imaging preparation state. The imaging preparation state is a state in which the driving unit 165 has executed imaging driving and a predetermined time has elapsed after the start of imaging driving. More specifically, the imaging preparation state is a state in which the initializing operation of the photoelectric conversion elements in the radiation detection apparatus 100 is performed. The initializing operation is driving of sequentially turning on the switching elements from the start row (y=0) to the last row (y=m) under the control of the driving unit 165. The initializing operation is performed to remove charges generated by a dark current generated in the photoelectric conversion element or by radiation irradiation. The initializing operation is an operation of performing a readout operation repetitively a plurality of times in an idling period in the preparatory stage before performing radiation imaging. The initializing operation is an operation of reading out image data having no radiation image. The initializing operation is repeated in a predetermined cycle for a predetermined time until the radiation detection apparatus 100 changes to the imaging possible state.

Upon completion of imaging preparation, the radiation detection apparatus 100 transits to step S203. The radiation detection apparatus 100 can also transit to the initialization state in step S201 in accordance with a preparation stop instruction from the imaging control apparatus 400. Step S203 represents that the radiation detection apparatus 100 is in the imaging possible state. The imaging possible state is a state in which the initializing operation of the photoelectric conversion elements in the radiation detection apparatus 100 has already been executed for a predetermined time. The imaging possible state is also a state in which obtainment, display, save, and the like of an image are possible in the imaging control apparatus 400, together with the above-described state in the radiation detection apparatus 100. The imaging possible state may be a state in which radiation imaging can be performed normally. If irradiation with radiation is performed in the imaging possible state, charges read out from the photoelectric conversion elements increase, and the radiation irradiation sensing unit 150 senses the irradiation with radiation.

After the start of imaging, the radiation detection apparatus 100 transits to step S204. Step S204 represents that the radiation detection apparatus 100 is in the ongoing imaging state. If the radiation irradiation sensing unit 150 determines the start of irradiation with radiation while the radiation detection apparatus 100 is in the imaging possible state (step S203), the initializing operation by the photoelectric conversion elements is stopped at the time. The photoelectric conversion elements shift to an operation of accumulating charges, and the radiation detection apparatus 100 changes to the ongoing imaging state (step S204). During accumulation of charges, all the switching elements are OFF under the control of the driving unit 165. If the accumulation of charges ends upon the lapse of a predetermined time, the photoelectric conversion elements shifts to actual reading. Actual reading is performed by sequentially turning on the switching elements from the start row (y=0) to the last row (y=m) under the control of the driving unit 165.

As a state of the radiation detection apparatus 100, there is also the imaging impossible state in step S205. The imaging impossible state is a state in which imaging is possible and to which the radiation detection apparatus 100 transits when the imaging control apparatus 400 is not ready yet. For example, when the radiation detection apparatus 100 is in the imaging possible state and receives a temporary impossible instruction from the imaging control apparatus 400, it shifts to the imaging impossible state. The imaging impossible state is a state in which the initializing operation of the photoelectric conversion elements has already been executed for a predetermined time, as in the imaging possible state, but the state can quickly return to the imaging possible state, unlike the imaging preparation state.

In the above example, when the radiation detection apparatus 100 is in the ongoing imaging state of step S204, it determines the start of irradiation with radiation, that is, senses irradiation with radiation. However, the radiation detection apparatus 100 may sense irradiation with radiation in the imaging preparation state of step S202 or the imaging impossible state of step S205. However, even if irradiation with radiation is sensed in these states, no appropriate image may be obtained.

Figure 4:
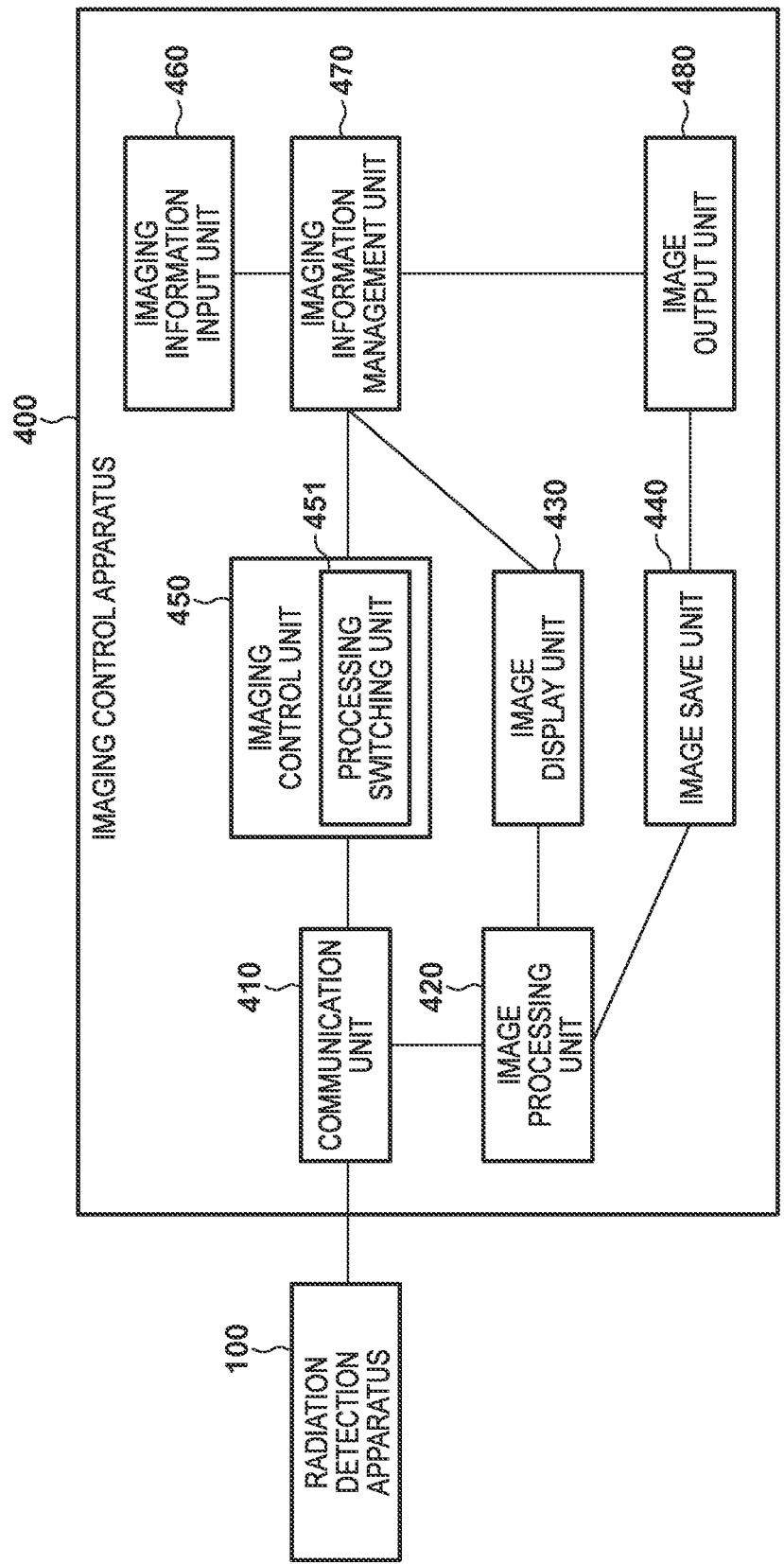
FIG. 4 is a block diagram showing an example of the arrangement of an imaging control apparatus according to the first embodiment.

FIG. 4 shows an example of the arrangement of the imaging control apparatus 400 according to this embodiment. The imaging control apparatus 400 according to this embodiment includes a communication unit 410, an image processing unit 420, an image display unit 430, an image save unit 440, an imaging control unit 450, an imaging information input unit 460, an imaging information management unit 470, and an image output unit 480. The communication unit 410 obtains an image from the radiation detection apparatus 100, and transmits/receives a control command. The image processing unit 420 performs image processing on an image obtained from the communication unit 410. The image display unit 430 performs control to display an image having undergone image processing by the image processing unit 420 on an external device such as a monitor. The image save unit 440 saves an image having undergone image processing by the image processing unit 420 in a hard disk or the like.

The imaging information input unit 460 is an interface for allowing a user to input imaging information (patient information/examination information) such as patient information, examination information, information of a radiation detection apparatus to be used, an imaging region, and a body build. The imaging information input unit 460 includes a touch panel formed integrally with a monitor. Alternatively, the imaging information input unit 460 may be another device that accepts an operation input from a user, including a keyboard and mouse connected to the imaging control apparatus 400. The imaging information includes, for example, information of a patient or object, and examination information of imaging conditions and the like. The information of the object includes information of the ID, name, age, and sex of the object. The examination information includes information of the examination ID, imaging count, imaging target region in every imaging, imaging method, and imaging direction. The imaging information management unit 470 manages imaging information input via the imaging information input unit 460. The imaging control unit 450 controls the radiation detection apparatus 100 based on information managed by the imaging information management unit 470. The image output unit 480 performs control of output to a printer, save medium, PACS, or the like.

The imaging control unit 450 according to this embodiment includes a processing switching unit 451. When it is determined that imaging information is complete in information managed by the imaging information management unit 470, the processing switching unit 451 instructs the radiation detection apparatus 100 via the communication unit 410 to transit to imaging preparation state S202. The imaging control unit 450 receives, from the radiation detection apparatus 100 via the communication unit 410 a predetermined time after this instruction, a notification that the radiation detection apparatus 100 has transited to imaging possible state S203. For example, in the imaging control apparatus 400, image obtainment sometimes becomes impossible for a reason to, for example, change imaging information or system settings. In such a case, the imaging control unit 450 determines to temporarily cancel the imaging possible state, and instructs the radiation detection apparatus 100 via the communication unit 410 to transit to imaging impossible state S205. After the radiation detection apparatus 100 transits to imaging possible state S203, it notifies the imaging control apparatus 400 via the communication unit 410 that imaging has started. Then, the imaging control apparatus 400 obtains an image via the communication unit 410.

In this manner, according to this embodiment, the imaging control unit 450 includes the processing switching unit 451 which determines whether imaging information managed by the imaging information management unit 470 is complete, and switches the method of obtaining an image to be held in the radiation detection apparatus 100, and the method of associating an image with imaging information.

Figure 9:
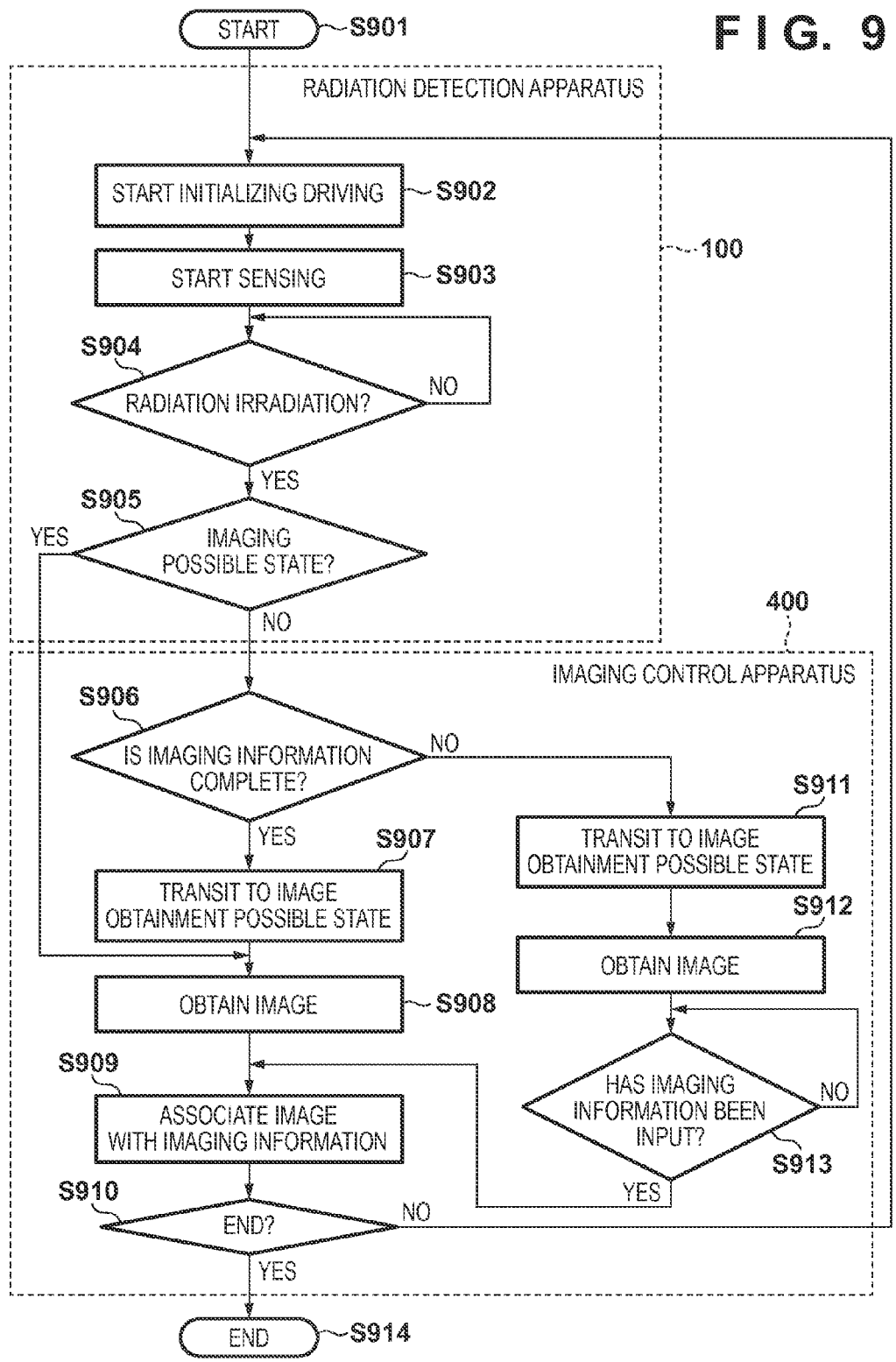
FIG. 9 is a flowchart showing the operation of the imaging system according to the first embodiment.

Next, an operation according to this embodiment will be explained with reference to FIG. 9. FIG. 9 is a flowchart showing the operation of the imaging system according to this embodiment. When the process starts (step S901), the radiation detection apparatus 100 starts initializing driving under the control of the driving unit 165 (step S902), and starts a radiation sensing operation (step S903). If the radiation irradiation sensing unit 150 senses irradiation with radiation (YES in step S904), the radiation detection apparatus 100 determines whether the radiation detection apparatus 100 is in imaging possible state S203 (step S905). If the radiation detection apparatus 100 is in imaging possible state S203 (YES in step S905), it notifies the imaging control apparatus 400 of normal exposure. In accordance with this notification, the imaging control apparatus 400 obtains an image from the radiation detection apparatus 100 via the communication unit 410 (step S908). The imaging control unit 450 of the imaging control apparatus 400 associates the image obtained via the communication unit 410 with imaging information managed by the imaging information management unit 470 (step S909). To the contrary, if the radiation detection apparatus 100 is not in imaging possible state S203, that is, the radiation detection apparatus 100 is in imaging preparation state S202 or imaging impossible state S205 (NO in step S905), it notifies the imaging control apparatus 400 of mis-exposure. The processing switching unit 451 of the imaging control apparatus 400 confirms whether imaging information managed by the imaging information management unit 470 is complete (step S906).

If the processing switching unit 451 confirms that imaging information is complete (YES in step S906), the imaging control apparatus 400 transits to an image obtainment possible state (step S907), and executes image obtainment via the communication unit 410 (step S908). The imaging control unit 450 associates the image obtained via the communication unit 410 with the imaging information managed by the imaging information management unit 470 (step S909). If the processing switching unit 451 confirms that imaging information is not complete (NO in step S906), the imaging control apparatus 400 transits to the image obtainment possible state (step S911), and executes image obtainment via the communication unit 410 (step S912). At the time of executing the processing in step S908 or S912, the imaging control apparatus 400 may execute image display or image save. At the time of image display, the imaging control apparatus 400 desirably displays an image at a tone capable of covering a wide dynamic range. This is because display in a dynamic range specialized in a specific region is not desirable, and an imaged region is first determined and then the user is allowed to select information of a region, body build, and the like.

Note that the confirmation of whether imaging information is complete (step S906) is not limited to the above example. For example, when a patient information input/examination selection screen is displayed in the imaging control apparatus 400, it may be confirmed that the imaging information is not complete (NO in step S906). When an imaging screen (screen for capturing and displaying a radiation image after designating patient information/examination information) or a region selection screen is displayed, it may be confirmed that the imaging information is complete (YES in step S906). The association between an image and imaging information is implemented by a data operation of, for example, setting the ID of imaging information in supplementary information of an image or the header of an image, or using an image ID included in imaging information as the ID of a corresponding image. An image including the ID of imaging information, and imaging information including the ID of the image are stored in the image save unit 440 or the like.

While referring to a displayed image, the user inputs patient information, examination information, information of a radiation detection apparatus to be used, and imaging information of an imaging region, body build, and the like to the imaging control apparatus 400 arbitrarily or in accordance with a system notification (step S913). Then, the image obtained by the radiation detection apparatus 100 and the imaging information are associated with each other (step S909). When only part of imaging information has been input in advance, the processing is performed according to the above-mentioned sequence coping with a case in which imaging information is not complete, but the partial imaging information input in advance is diverted. If imaging is not performed again (YES in step S910), the process ends (step S914).

As described above, according to the first embodiment, when mis-exposure is performed, the imaging control apparatus 400 associates an obtained image with imaging information after the imaging information is input. That is, if the user inputs imaging information even for a captured image obtained by mis-exposure, the imaging control apparatus 400 saves the captured image and the imaging information in association with each other. Thus, even for a captured image obtained by mis-exposure, the user can manage the image in the imaging control apparatus 400, and the necessity of re-imaging can be suppressed.

[Modification 1]

Figure 10:
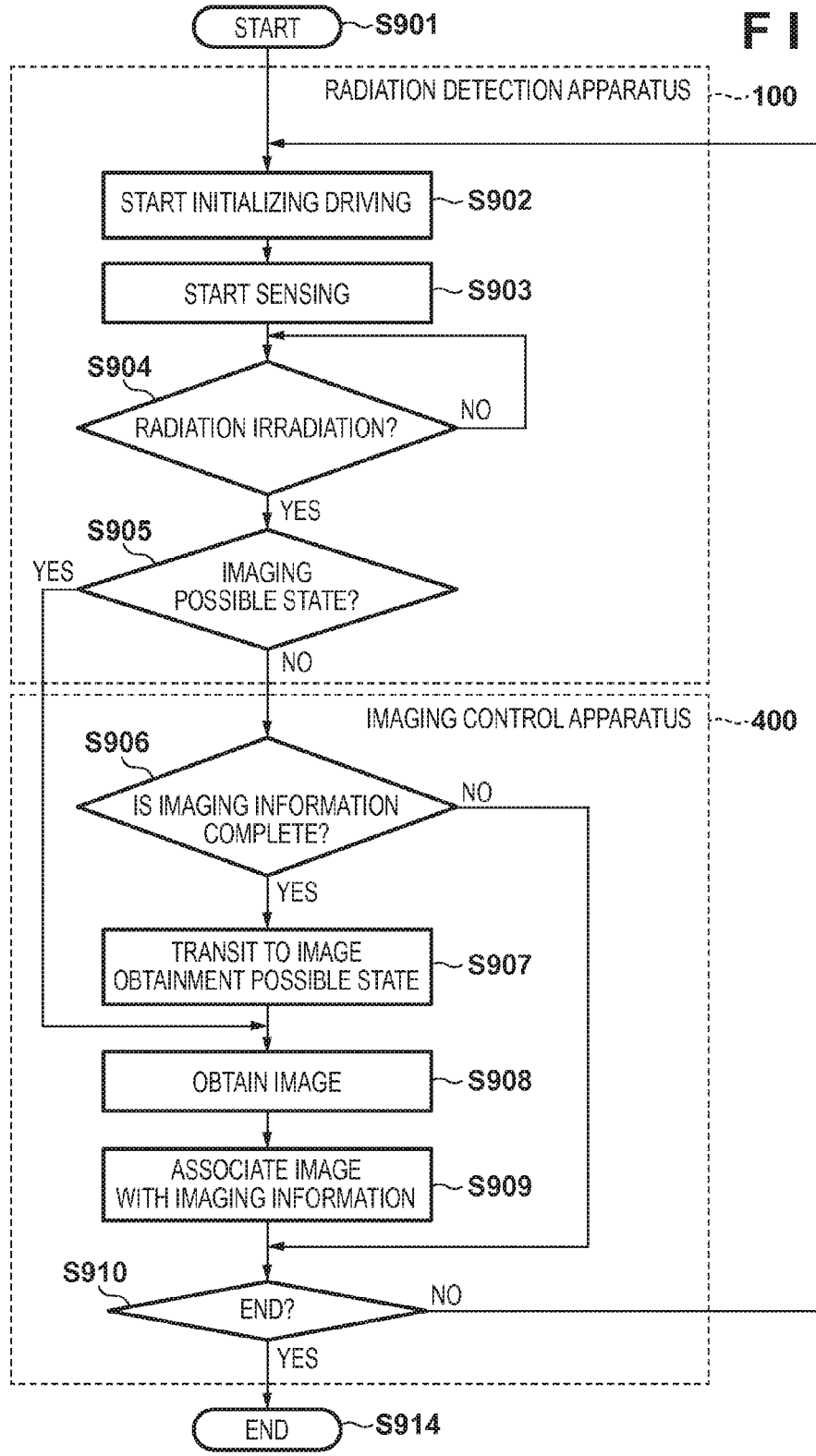
FIG. 10 is a flowchart showing the operation of the imaging system according to modification 1 of the first embodiment.

An operation according to modification 1 of the first embodiment will be explained with reference to FIG. 10. FIG. 10 is a flowchart showing the operation of the imaging system according to this modification. Processes up to confirmation (step S906) of whether imaging information is complete are the same as those in FIG. 9 explained in the first embodiment. Processing when imaging information is complete (YES in step S906) is also the same. However, when imaging information is not complete (NO in step S906), the imaging control apparatus 400 advances to step S910 without executing image obtainment and the like, and if imaging is not performed again (YES in step S910), the process ends (step S914).

As described above, according to modification 1, when mis-exposure is performed and imaging information is not complete in the imaging control apparatus 400, the imaging control apparatus 400 does not obtain an image from the radiation detection apparatus 100. That is, only when imaging information is complete even for a captured image obtained by mis-exposure, the imaging control apparatus 400 saves the captured image and the imaging information in association with each other. Hence, even for a captured image obtained by mis-exposure, the user can manage the image in the imaging control apparatus 400 on condition that there is imaging information, and the necessity of re-imaging can be suppressed.

[Modification 2]

Figure 11:
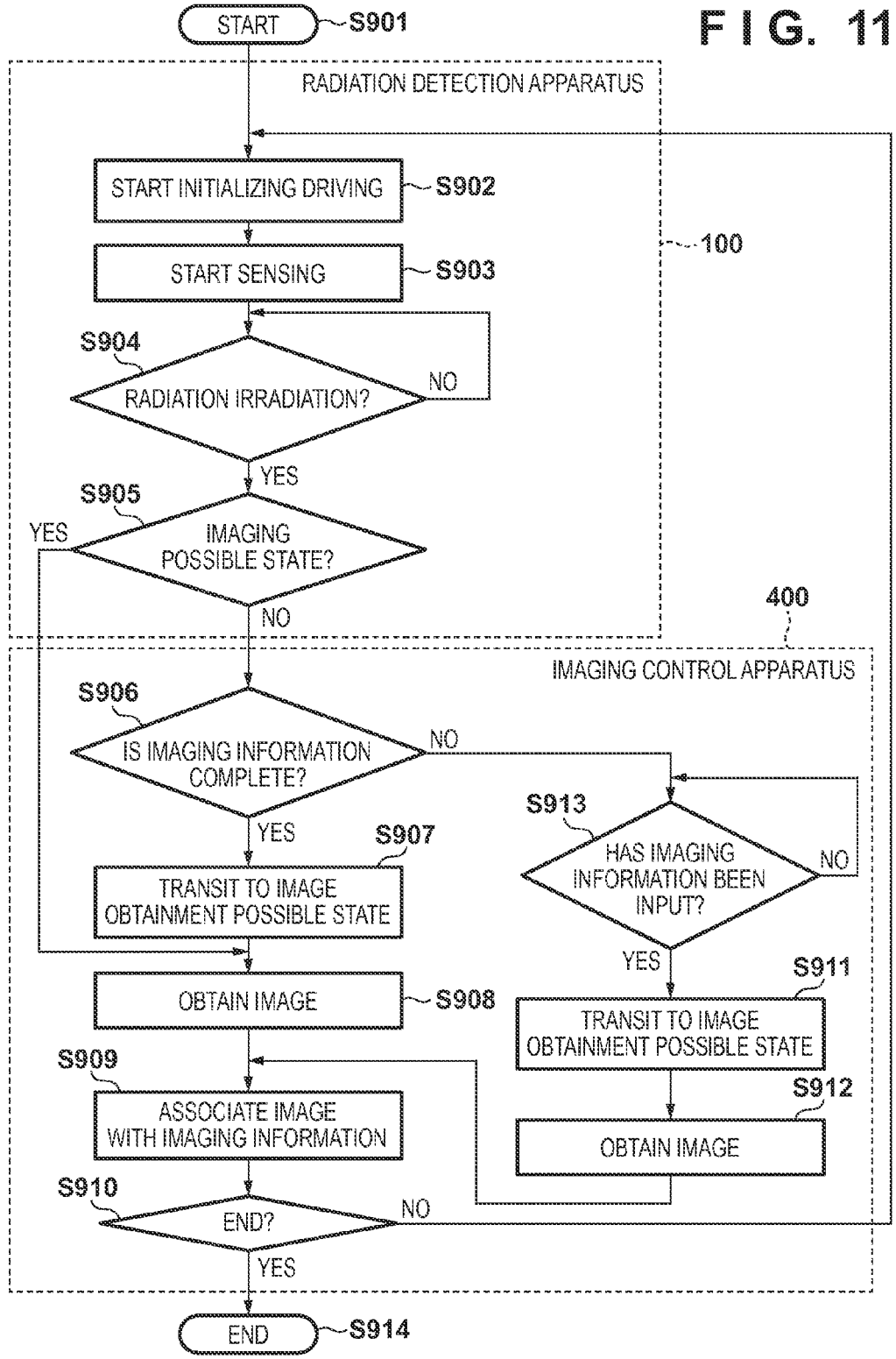
FIG. 11 is a flowchart showing the operation of the imaging system according to modification 2 of the first embodiment.

An operation according to modification 2 of the first embodiment will be explained with reference to FIG. 11. FIG. 11 is a flowchart showing the operation of the imaging system according to this modification. Processes up to confirmation (step S906) of whether imaging information is complete are the same as those in FIG. 9 explained in the first embodiment. Processing when imaging information is complete (YES in step S906) is also the same. However, when imaging information is not complete (NO in step S906), the order of steps S911 to S913 of FIG. 9 explained in the first embodiment is different. More specifically, the user executes input (step S913) of imaging information to the imaging control apparatus 400 arbitrarily or in accordance with a system notification. After that, the process transits to the image obtainment possible state (step S912), and image obtainment is executed via the communication unit 410 (step S911). The imaging control unit 450 associates the image obtained via the communication unit 410 with imaging information (step S909). If imaging is not performed again (YES in step S910), the process ends (step S914).

As described above, according to modification 2, when mis-exposure is performed and imaging information is not complete in the imaging control apparatus 400, the imaging control apparatus 400 transits to the image obtainment possible state after waiting for input of imaging information by the user. That is, even for a captured image obtained by mis-exposure, if the user inputs imaging information, the imaging control apparatus 400 saves the captured image and the imaging information in association with each other. Even for the captured image obtained by mis-exposure, the user can manage the image in the imaging control apparatus 400, and the necessity of re-imaging can be suppressed.

[Modification 3]

Figure 5:
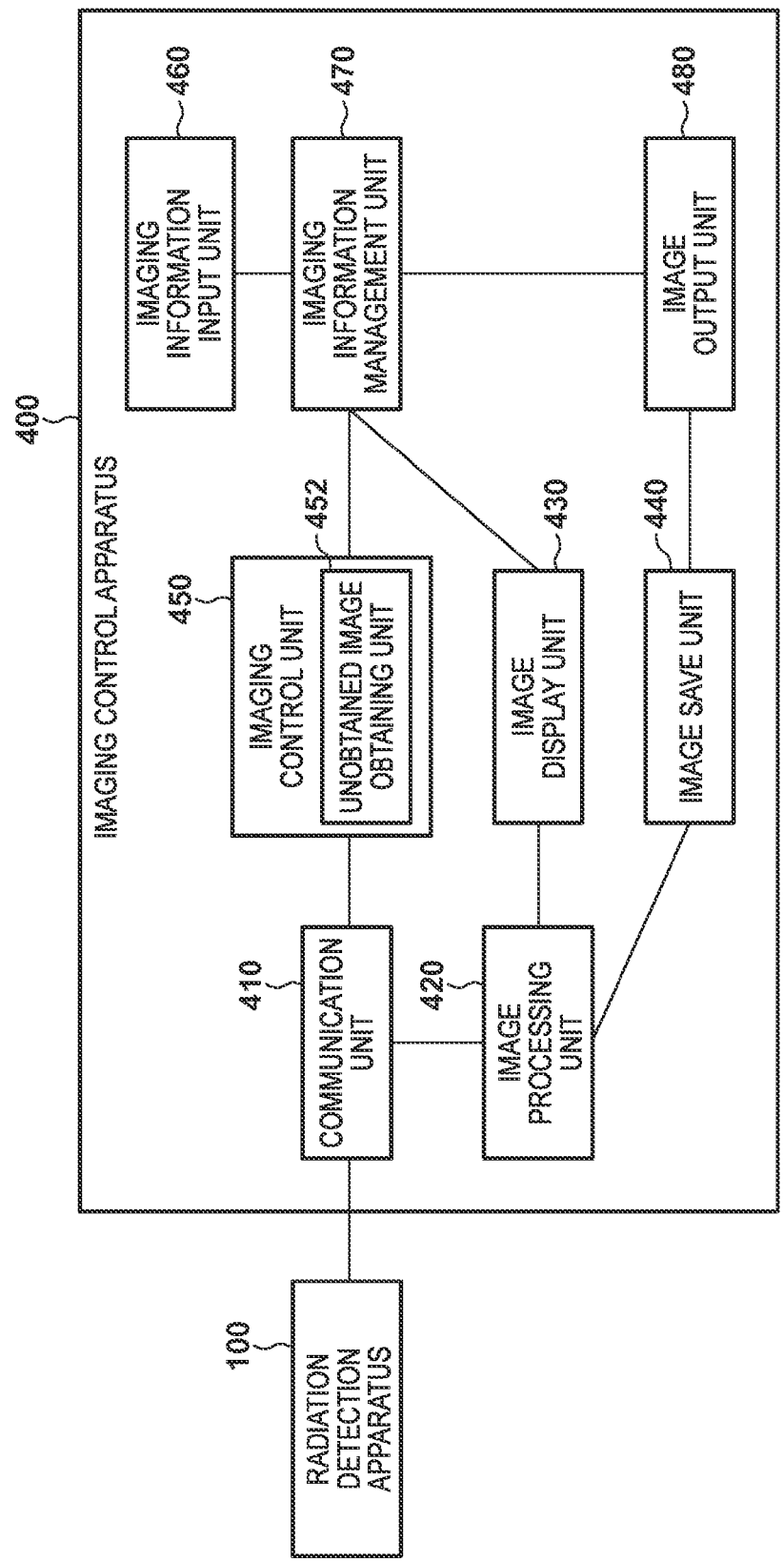
FIG. 5 is a block diagram showing an example of the arrangement of the imaging control apparatus according to modification 3 of the first embodiment.

The arrangement and operation of the imaging control apparatus 400 according to modification 3 of the first embodiment will be explained with reference to FIGS. 5 and 12. FIG. 5 is a block diagram showing an example of the arrangement of the imaging control apparatus 400 according to this modification. The imaging control apparatus 400 according to this modification is partially different from that in FIG. 4 explained in the first embodiment, and the imaging control unit 450 includes an unobtained image obtaining unit 452. The unobtained image obtaining unit 452 confirms the presence/absence of an image not obtained by the imaging control apparatus 400 though irradiation with radiation has been sensed in the radiation detection apparatus 100. The confirmation timing is the timing when a connection between the imaging control apparatus 400 and the radiation detection apparatus 100 is established. When the unobtained image obtaining unit 452 confirms that there is an unobtained image, the imaging control apparatus 400 performs image obtainment and association with imaging information.

Figure 12:
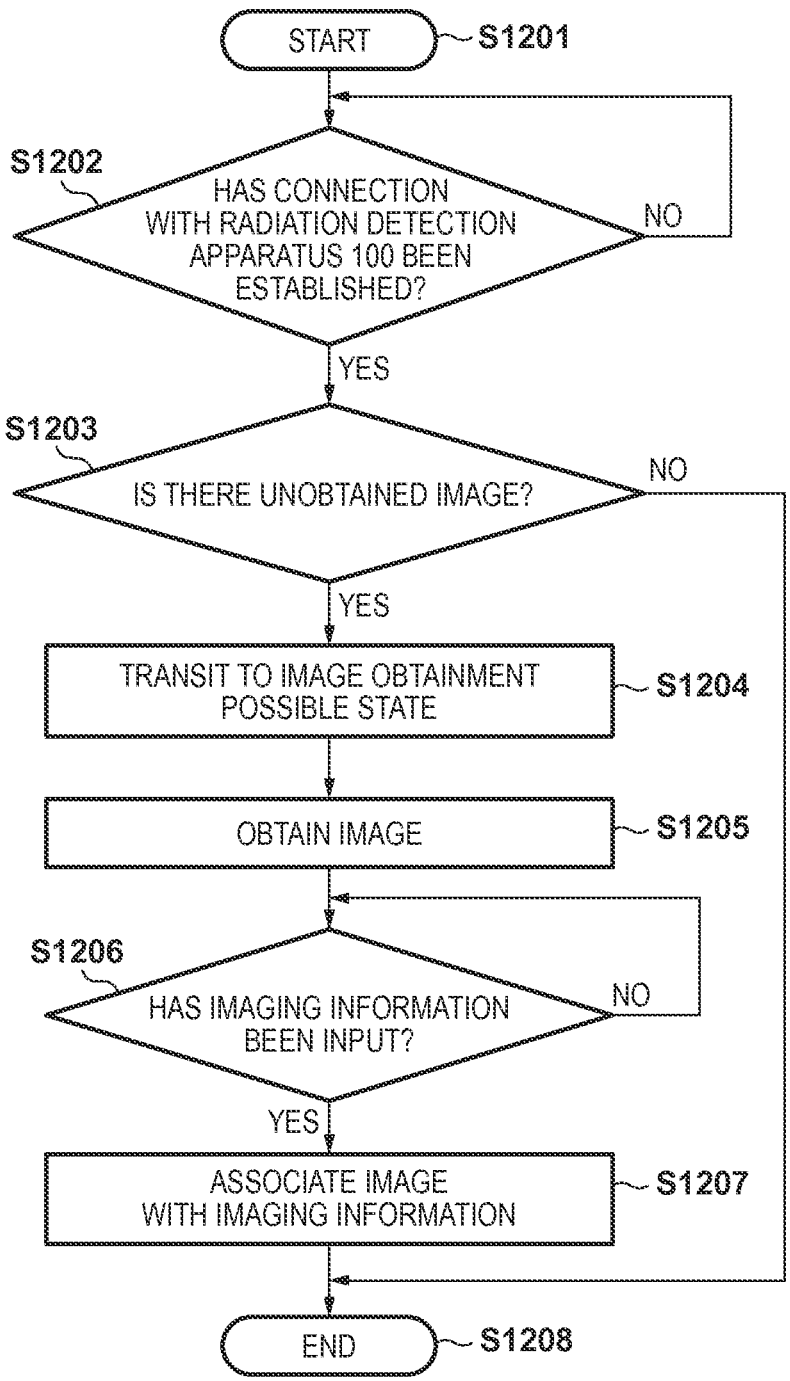
FIG. 12 is a flowchart showing the operation of the imaging system according to modification 3 of the first embodiment.

FIG. 12 is a flowchart showing the operation of the imaging control apparatus 400 according to this modification. Assume that the radiation detection apparatus 100 and the imaging control apparatus 400 are in the disconnected state, irradiation with radiation has been performed, and the radiation detection apparatus 100 has performed radiation detection and imaging in advance. When the process starts (step S1201), the imaging control apparatus 400 confirms whether a connection with the radiation detection apparatus 100 has been established (step S1202). If the establishment is confirmed (YES in step S1202), the unobtained image obtaining unit 452 of the imaging control apparatus 400 confirms the presence/absence of an image which has not been obtained yet by the imaging control apparatus 400 though irradiation with radiation has been sensed (step S1203). In this confirmation, first, the radiation detection apparatus 100 notifies the imaging control apparatus 400 that irradiation with radiation has been sensed. This notification includes information (for example, identification information) of an image already captured in the radiation detection apparatus 100. Based on information of the already captured image that has been received from the radiation detection apparatus 100, the imaging control apparatus 400 confirms the image which has not been obtained yet by the imaging control apparatus 400. If there is no unobtained image (NO in step S1203), the process ends (step S1208). If there is an unobtained image (YES in step S1203), the imaging control apparatus 400 transits to the image obtainment possible state (step S1204), and executes image obtainment (step S1205) via the communication unit 410.

The processes in step S1205 and subsequent steps are the same as those in FIG. 9 explained in the first embodiment. While referring to a displayed image, the user inputs patient information, examination information, information of a radiation detection unit to be used, and imaging information of an imaging region, body build, and the like arbitrarily or in accordance with a system notification (step S1206). The imaging control unit 450 of the imaging control apparatus 400 associates the image with the imaging information (step S1207), and ends the process (step S1208). Note that the timing of the processing (step S1203) of confirming the presence/absence of an unobtained image by the imaging control apparatus 400 is not limited to the timing after confirmation of connection establishment with the radiation detection apparatus 100.

Also in this modification, the imaging control apparatus 400 may perform image display and image save, as in the first embodiment. At the time of image display, an image is desirably displayed at a tone capable of covering a wide dynamic range. This is because display in a dynamic range specialized in a specific region is not desirable, and an imaged region is first determined and then the user is allowed to select information of a region, body build, and the like. When only part of imaging information has been input in advance, the processing is performed according to the above-mentioned sequence coping with a case in which imaging information is not complete, but the partial imaging information input in advance is diverted.

As described above, according to modification 3, the imaging control apparatus 400 obtains an image which has already been captured by the radiation detection apparatus 100 but has not been held yet by the imaging control apparatus 400 itself. The imaging control apparatus 400 then associates the captured image with imaging information. The user can therefore manage images captured by the radiation detection apparatus 100 without missing them. When a given image has already been captured by the radiation detection apparatus 100 but is not managed by the imaging control apparatus 400, re-imaging to be executed for this reason can be avoided.

[Modification 4]

Figure 13:
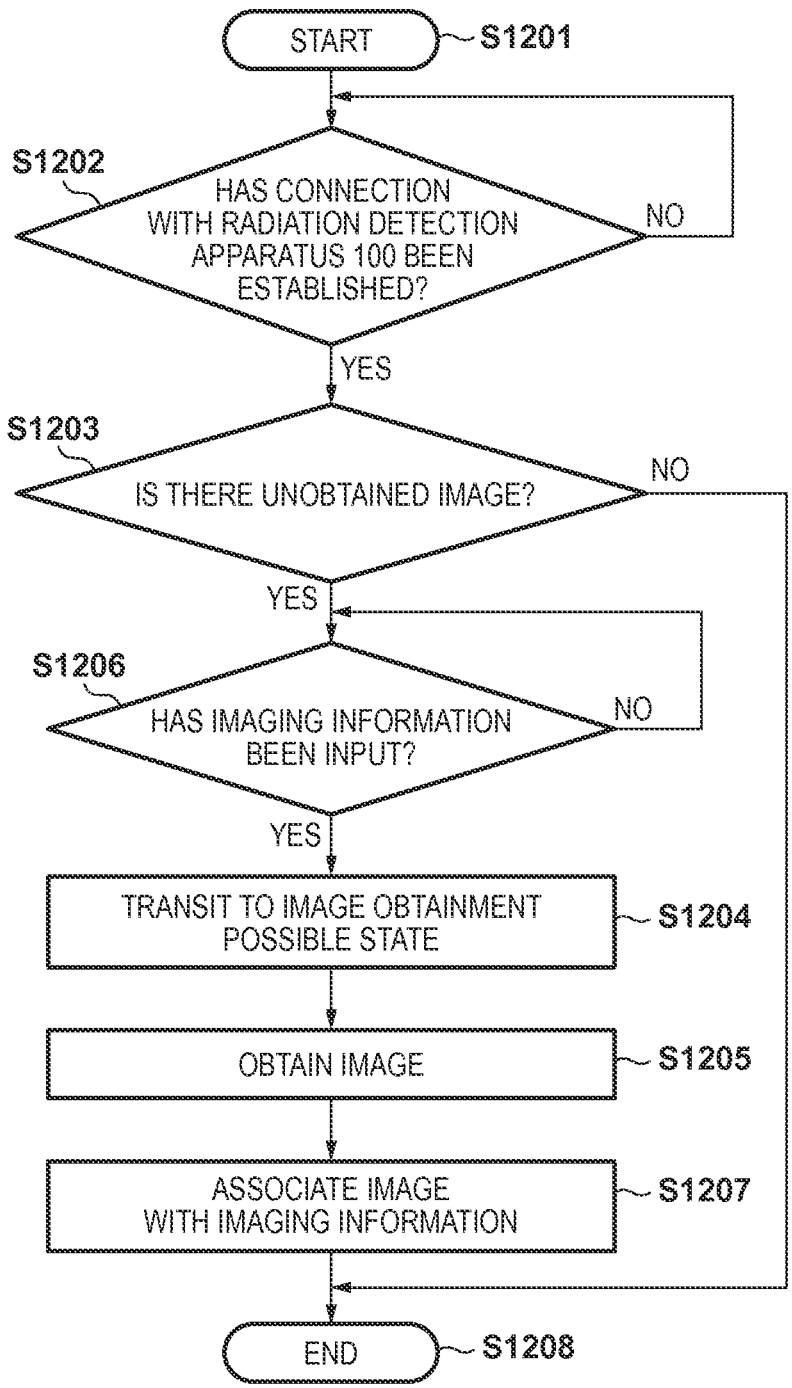
FIG. 13 is a flowchart showing the operation of the imaging system according to modification 4 of the first embodiment.

An operation according to modification 4 of the first embodiment will be explained with reference to FIG. 13. FIG. 13 is a flowchart showing the operation of the imaging control apparatus 400 according to this modification. Processes up to confirmation (step S1203) of the presence/absence of an image which has not been obtained yet though irradiation with radiation has been sensed are the same as those in FIG. 12 explained in modification 3. Processing when there is no such image (NO in step S1203) is also the same. However, when there is an unobtained image (YES in step S1203), the order of steps S1204 to S1206 in FIG. 13 is different. More specifically, the user executes input (step S1206) of imaging information arbitrarily or in accordance with a system notification. After that, the imaging control apparatus 400 transits to the image obtainment possible state (step S1204), executes image obtainment via the communication unit 410 (step S1205), associates the image with imaging information (step S1207), and ends the process (step S1208).

As described above, according to modification 4, after the imaging control apparatus 400 obtains an image which has already been captured by the radiation detection apparatus 100 and has not been held yet by the imaging control apparatus 400 itself, it transits to the image obtainment possible stage after waiting for input of imaging information by the user. Therefore, the user does not miss a captured image, and the imaging control apparatus 400 obtains and saves only an image associated with imaging information. The user can easily manage the image saved in the imaging control apparatus 400. In addition, when a given image has been captured by the radiation detection apparatus 100 but is not managed by the imaging control apparatus 400, re-imaging to be executed for this reason can be avoided.

[Modification 5]

Figure 6:
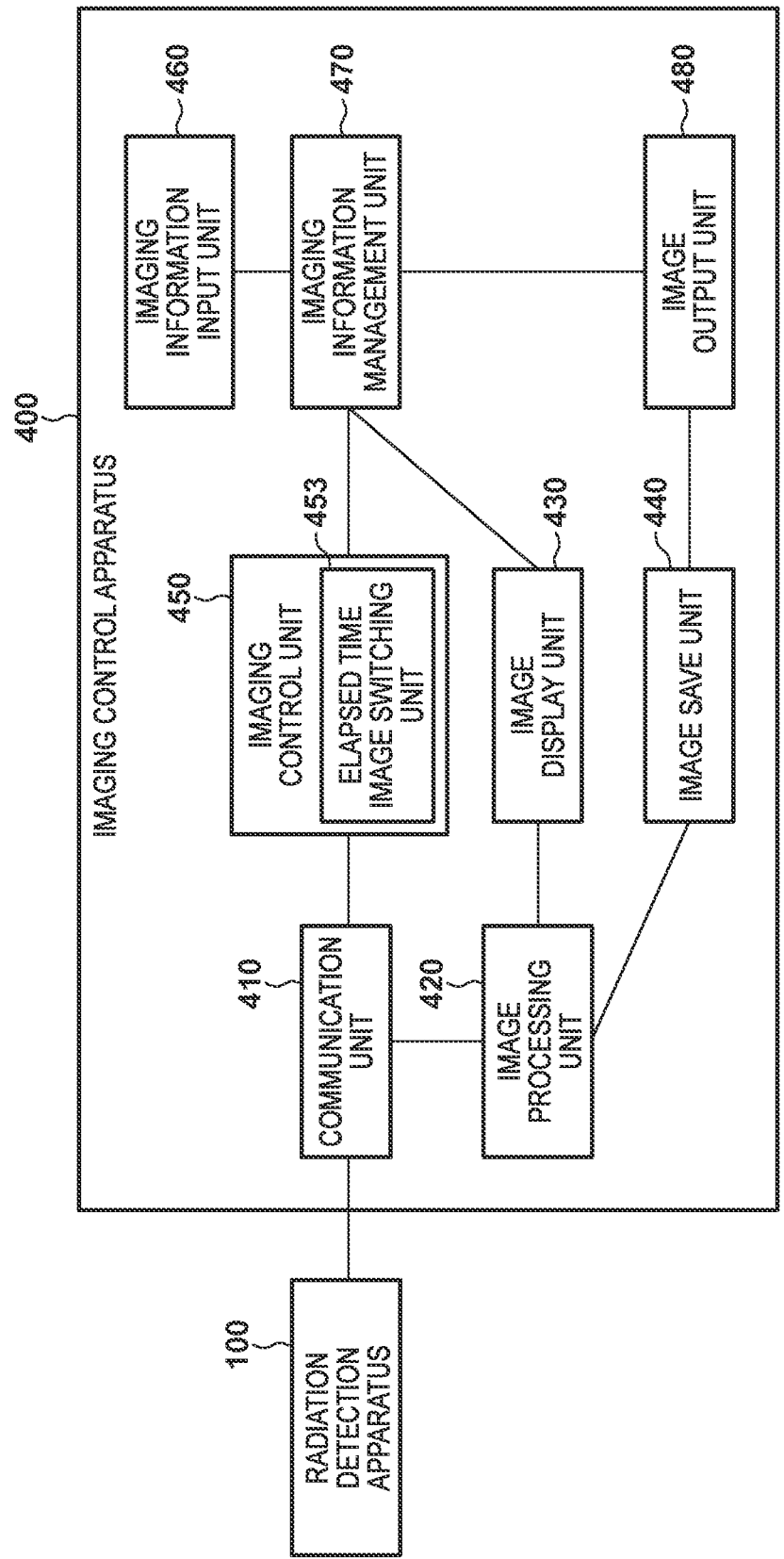
FIG. 6 is a block diagram showing an example of the arrangement of the imaging control apparatus according to modification 5 of the first embodiment.

The arrangement and operation of the imaging control apparatus 400 according to modification 5 of the first embodiment will be explained with reference to FIGS. 6 and 14. FIG. 6 shows an example of the arrangement of the imaging control apparatus 400 according to this modification. The imaging control apparatus 400 according to this modification is partially different from those in FIGS. 4 and 5, and the imaging control unit 450 includes an elapsed time image switching unit 453. When the radiation detection apparatus 100 is not in the imaging possible state, that is, is in imaging preparation state S202 or imaging impossible state S205, if the radiation detection apparatus 100 senses irradiation with radiation, the elapsed time image switching unit 453 determines whether to obtain an image, based on the time elapsed after the start of initialization.

Figure 14:
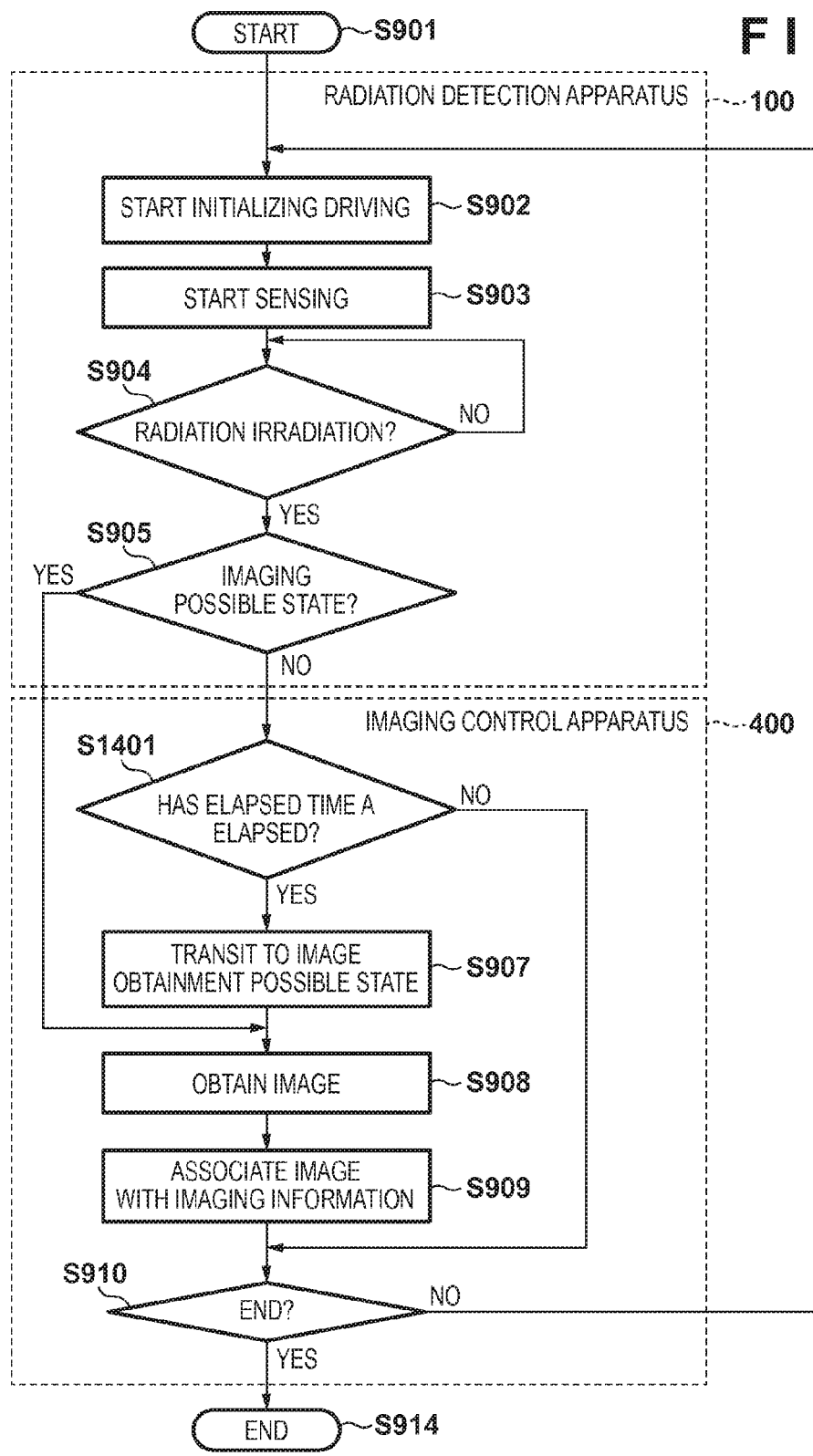
FIG. 14 is a flowchart showing the operation of the imaging system according to modification 5 of the first embodiment.

FIG. 14 is a flowchart showing the operation of the imaging system according to this modification. Processes up to confirmation (step S905) of whether the radiation detection apparatus 100 is in the imaging possible state are the same as those in FIG. 10 explained in modification 1. However, if the radiation detection apparatus 100 is not in the imaging possible state (NO in step S905), the elapsed time image switching unit 453 determines whether an elapsed time A has elapsed after the start of initialization (step S1401). Note that the radiation detection apparatus 100 may notify the imaging control apparatus 400 of the initialization start time at the start of initializing driving in step S902. The elapsed time A is, for example, 10 sec and is equal to the time when the radiation detection apparatus 100 transits from imaging preparation state S202 to imaging possible state S203. When this elapsed time has elapsed, the quality of an image to be captured by the radiation detection apparatus 100 is equal to that of an image to be captured in imaging possible state S203.

When, therefore, the predetermined elapsed time has elapsed (YES in step S1401), even if the radiation detection apparatus 100 is in imaging impossible state S205, the radiation detection apparatus 100 is free from a problem in imaging, and the imaging control apparatus 400 transits to the image obtainment possible state (step S907). The imaging control apparatus 400 obtains an image (step S908), and associates the image with imaging information by a method described in one of the first embodiment and modification 1 to modification 4 (step S909). If imaging is not performed again (YES in step S910), the process ends (step S914).

As described above, according to modification 5, when the predetermined time has elapsed after the initializing operation in the radiation detection apparatus 100, the imaging control apparatus 400 determines that there is no problem in image quality, and obtains a captured image from the radiation detection apparatus 100. That is, even if the user does not accurately measure the time elapsed after the initializing operation in the radiation detection apparatus 100, the imaging control apparatus 400 measures this time and determines whether an image free from a problem in image quality can be obtained. Wasteful re-imaging to be performed for the reason of inaccurate time measurement by the user can be avoided.

[Modification 6]

Figure 15:
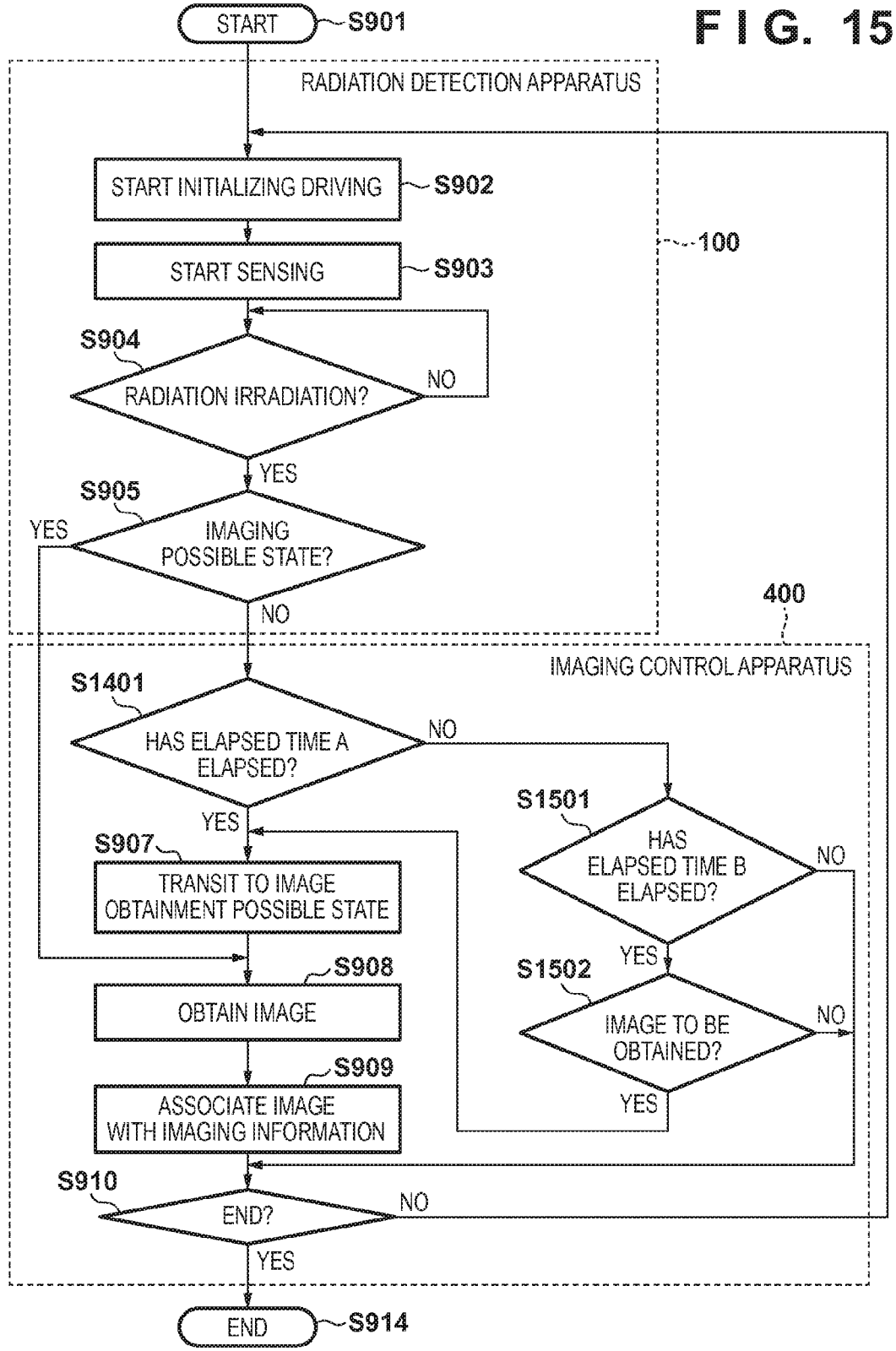
FIG. 15 is a flowchart showing the operation of the imaging system according to modification 6 of the first embodiment.

An operation according to modification 6 of the first embodiment will be explained with reference to FIG. 15. FIG. 15 is a flowchart showing the operation of the imaging system according to this modification. Processes up to confirmation (step S1401) of whether the elapsed time A has elapsed are the same as those in FIG. 14 explained in modification 5. Processing when the elapsed time has elapsed (YES in step S1401) is also the same. However, processing when the elapsed time A has not elapsed (NO in step S1401) is different. If the elapsed time A has not elapsed (NO in step S1401), the elapsed time image switching unit 453 determines whether an elapsed time B shorter than the elapsed time A has elapsed (step S1501). For example, it can be determined that when A is equal to or longer than 10 sec, an image free from a problem in image quality can be obtained, when B is equal to or longer than 5 sec, an image can be effective depending on the purpose of the user, and when the time is shorter than 5 sec, the image quality cannot be guaranteed.

Hence, if the elapsed time B has elapsed (YES in step S1501), the imaging control apparatus 400 prompts the user to determine whether to obtain an image (step S1502). If the user wants to obtain an image (YES in step S1502), the process shifts to the image obtaining sequence (steps S907 to S909). If the user determines not to obtain an image (NO in step S1502), the imaging control apparatus 400 does not obtain an image.

As described above, according to modification 6, when the user wants to obtain an image in the stage in which an effective image can be obtained, the imaging control apparatus 400 obtains an image from the radiation detection apparatus 100. That is, even if the user does not accurately measure the time elapsed after the initializing operation in the radiation detection apparatus 100, the imaging control apparatus 400 measures this time and determines whether an effective image can be obtained, and then the user determines whether to obtain an image. Wasteful re-imaging to be performed against the user intention for the reason of inaccurate time measurement by the user can therefore be avoided.

[Modification 7]

Figure 16:
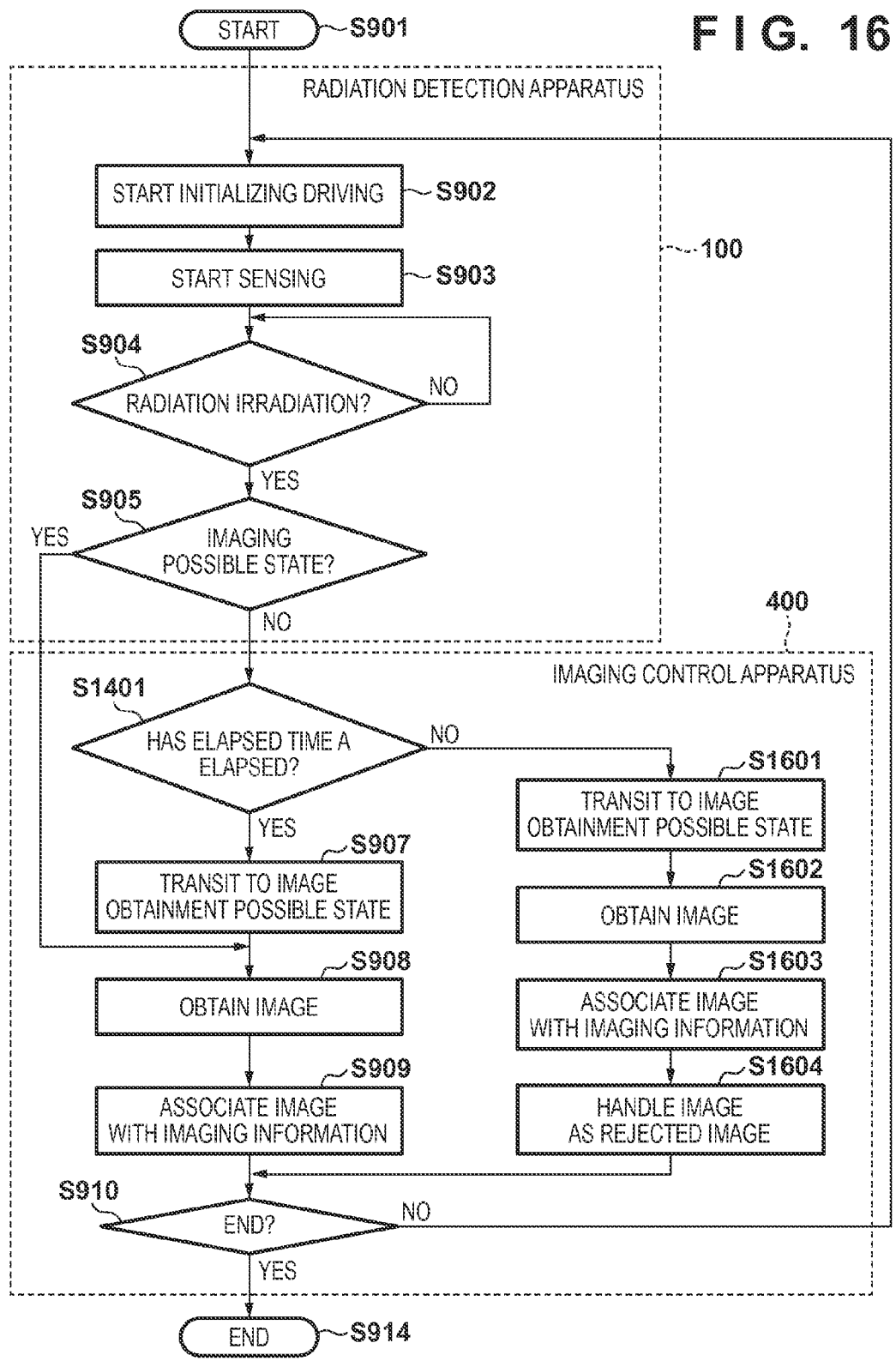
FIG. 16 is a flowchart showing the operation of the imaging system according to modification 7 of the first embodiment.

An operation according to modification 7 of the first embodiment will be explained with reference to FIG. 16. FIG. 16 is a flowchart showing the operation of the imaging system according to this modification. Processes up to confirmation (step S1401) of whether the elapsed time A has elapsed are the same as those in FIGS. 14 and 15 explained in modification 5 and modification 6. Processing when the elapsed time has elapsed (YES in step S1401) is also the same. However, processing when the elapsed time A has not elapsed (NO in step S1401) is different. If the elapsed time A has not elapsed (NO in step S1401), the process shifts to the image obtaining sequence (steps S1601 to S1603), as in the case in which the elapsed time A has elapsed (YES in step S1401). Further, the imaging control apparatus 400 handles the obtained image as a rejected image (failed image as a result of a failure by various causes generated at the time of capturing a radiation image: a rejected image is transferred to neither the PACS nor the printer). The imaging control apparatus 400 displays the rejected image on the screen in an expression indicating the failure by superimposing a x mark on the image. The user can refer to the rejected image, and if he checks the image and determines that it is an effective image, can cancel the rejection and return the rejected image to a normal image.

According to modification 7, while representing that an image is highly likely to be ineffective for the user, the imaging control apparatus 400 can handle the image as a normal image if the effectiveness is confirmed. The imaging control apparatus 400 handles the image as a rejected image, can save information of the dose used, and can exploit it even in statistical information of dose management. In the case of a system capable of inputting and storing the reason why an image becomes a rejected image, it may be described in this reason that the elapsed time after the start of initialization has not reached a predetermined time and no satisfactory image quality may be guaranteed. The elapsed time after the start of initialization may also be described in this reason.

As described above, according to modification 7, even when a predetermined time has not elapsed after the initializing operation in the radiation detection apparatus 100, the imaging control apparatus 400 obtains an image from the radiation detection apparatus 100, and handles the obtained image as a rejected image. The user can avoid wasteful re-imaging on condition that a poor-quality image is handled as a rejected image in the imaging control apparatus 400.

[Modification 8]

Figure 7:
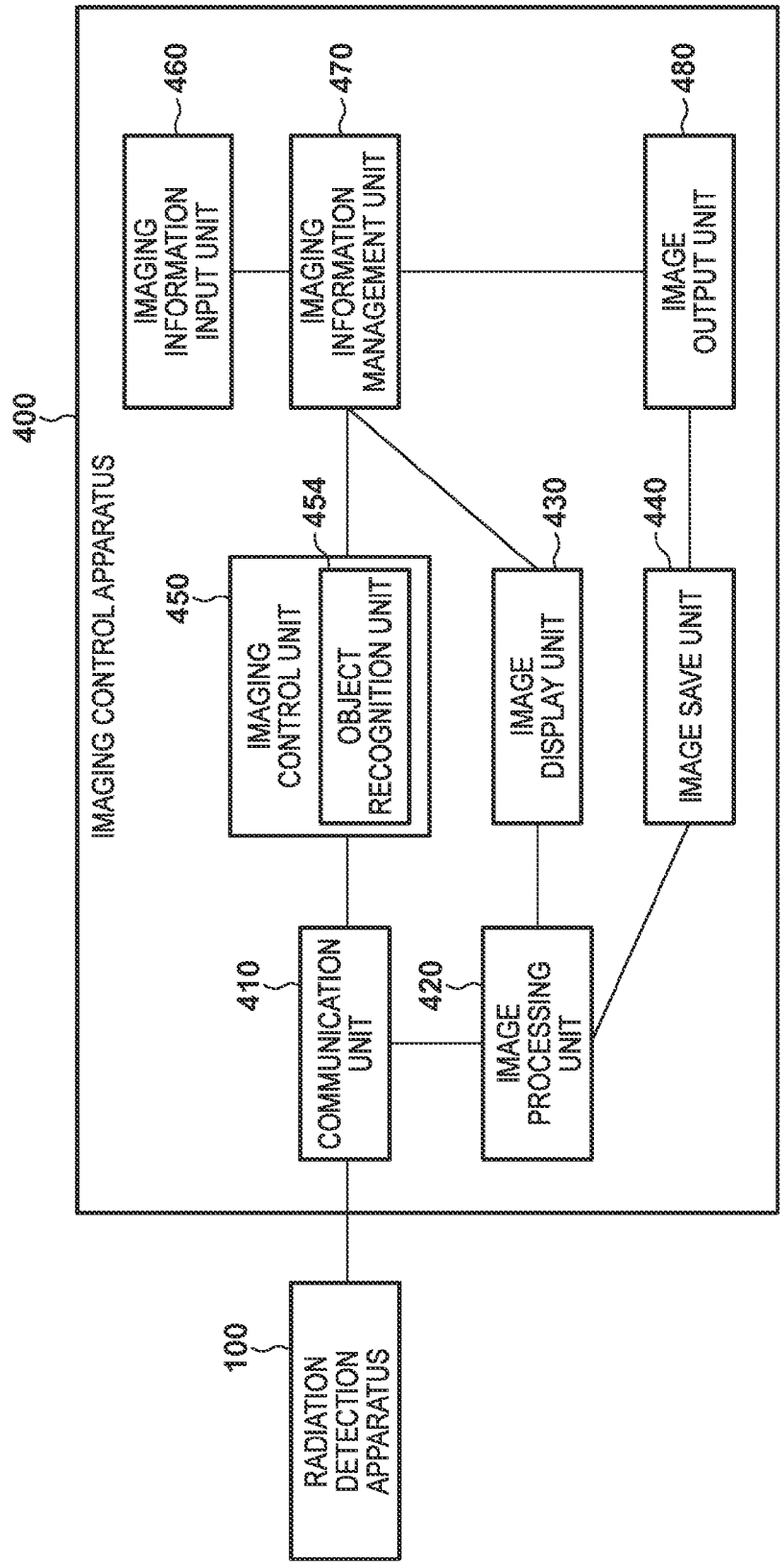
FIG. 7 is a block diagram showing an example of the arrangement of the imaging control apparatus according to modification 7 of the first embodiment.
Figure 17:
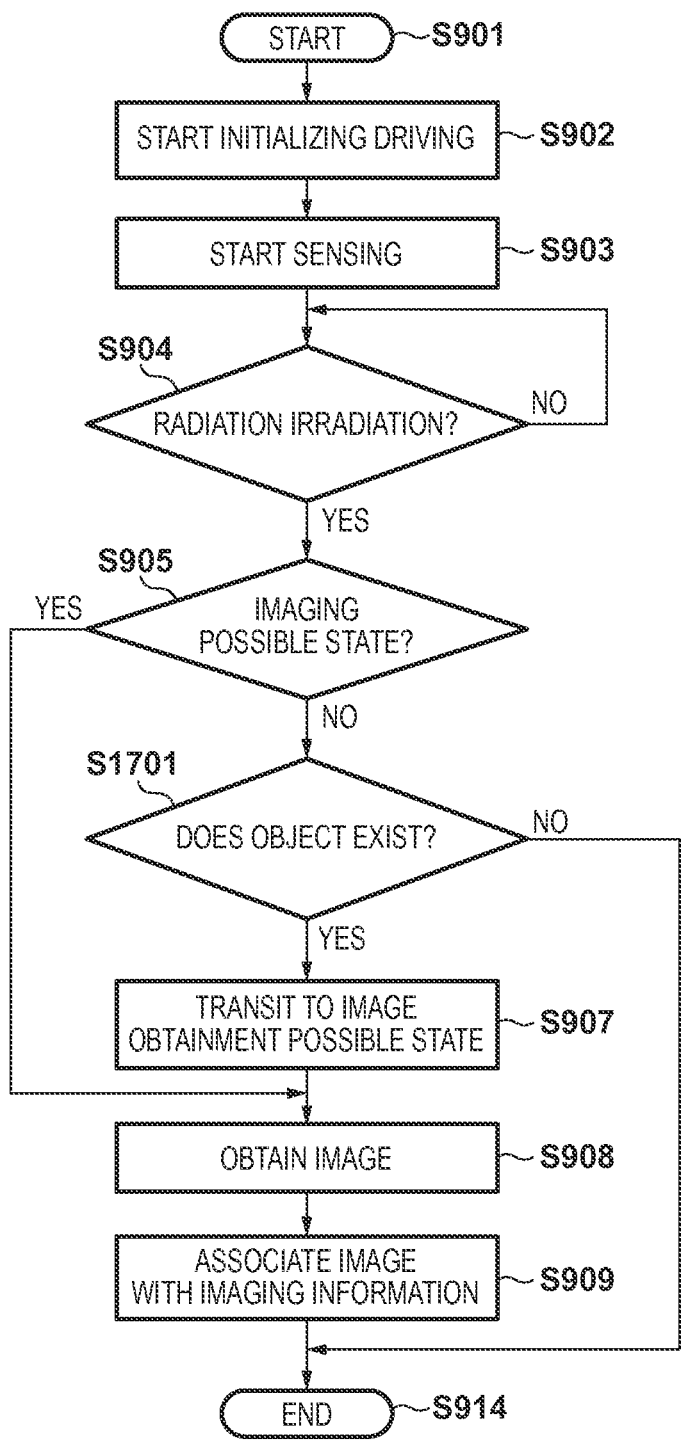
FIG. 17 is a flowchart showing the operation of the imaging system according to modification 8 of the first embodiment.

The arrangement and operation of the imaging control apparatus 400 according to modification 8 of the first embodiment will be explained with reference to FIGS. 7 and 17. FIG. 7 shows an example of the arrangement of the imaging control apparatus 400 according to this modification. The imaging control apparatus 400 according to this modification is partially different from those in FIGS. 4 to 6, and the imaging control unit 450 includes an object recognition unit 454 capable of recognizing whether the object 300 exists. Here, the object 300 is a human in the case of medical equipment, an animal in the case of medical equipment for animals, and a matter in the case of inspection equipment as for nondestructive inspection.

An operation according to this modification will be explained with reference to FIG. 17. FIG. 17 is a flowchart showing the operation of the imaging control apparatus 400 according to this modification. Processes up to determination (step S905) of whether the radiation detection apparatus 100 is in the imaging possible state are the same as those in FIG. 10 explained in modification 1. However, processing when the radiation detection apparatus 100 is not in the imaging possible state (NO in step S905) is different. If the radiation detection apparatus 100 is not in the imaging possible state (NO in step S905), the object recognition unit 454 determines, by a predetermined object recognition method, whether an object exists in a captured image (step S1701). As the object recognition method by the object recognition unit 454, there is a determination method based on image processing of, for example, extracting the histogram of an image, the edge of an object, or the like, or a determining method using a contact sensor. Further, as the object recognition method, there are conceivable a determination method using an infrared remote sensor or the like, and a determination method based on information from a dosemeter or phototimer. Another recognition method may also be used. The object recognition unit 454 may obtain a rough image from the radiation detection apparatus 100 and perform such analysis. Note that the object recognition unit 454 may receive, from the radiation detection apparatus 100, the result of analyzing a captured image, and determine whether an object exists in the captured image.

If an object exists (YES in step S1701), the process shifts to the image obtaining sequence (steps S907 to S909). If no object exists (NO in step S1701), image obtainment is not performed. If an object exists, the imaging control apparatus 400 may handle the image as a rejected image, as described in modification 7. This image is handled as the rejected image because when an object exists, it is necessary to perform dose management, and hold the image or hold it as a rejected image. To the contrary, if no object exists, erroneous mis-exposure or erroneous detection by the radiation detection apparatus is highly likely to have been performed, and no image need be held.

As described above, according to modification 8, when an object exists, the imaging control apparatus 400 obtains a captured image. Even if the image quality is poor in the imaging control apparatus 400, the user can obtain and save an image in which the object exists, and avoid wasteful re-imaging.

[Modification 9]

Figure 8:
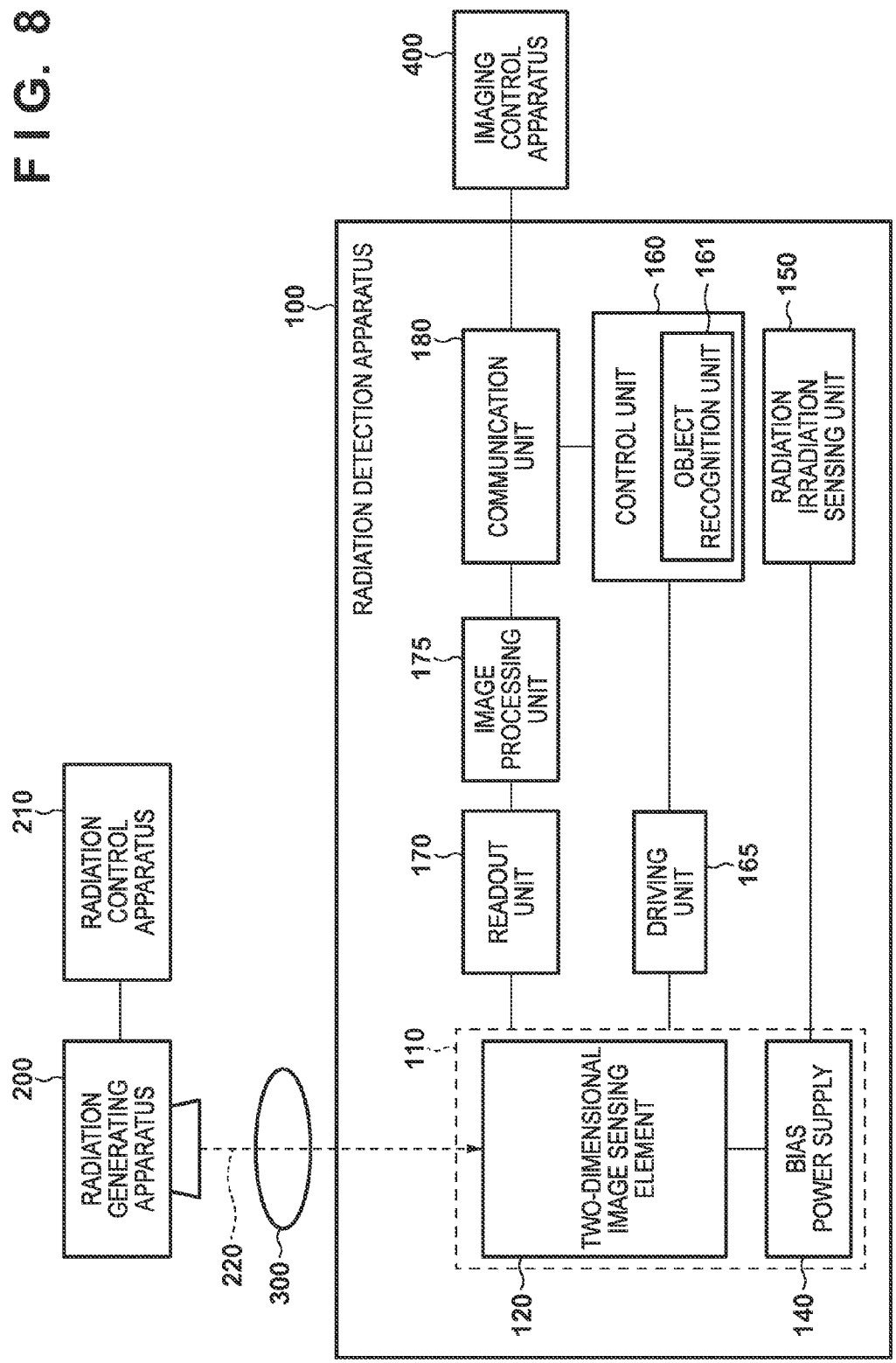
FIG. 8 is a block diagram showing an example of the arrangement of the imaging control apparatus according to modification 8 of the first embodiment.
Figure 18:
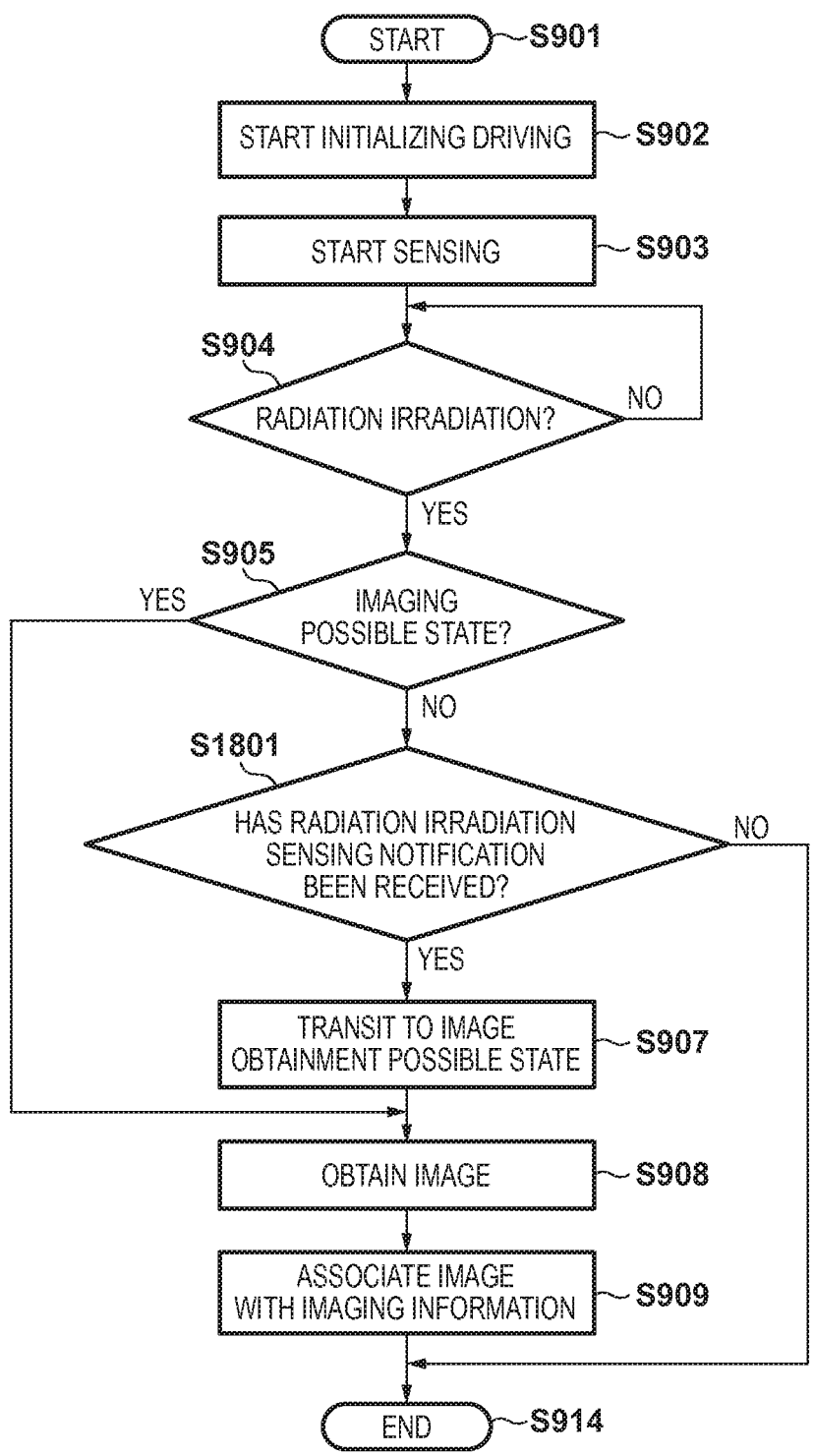
FIG. 18 is a flowchart showing the operation of the imaging system according to modification 9 of the first embodiment.

The arrangement and operation of the imaging control apparatus 400 according to modification 9 of the first embodiment will be explained with reference to FIGS. 8 and 18. FIG. 8 shows an example of the arrangement of the imaging control apparatus 400 according to this modification. In the radiation detection apparatus 100 according to this modification, an object recognition unit 161 equivalent to the object recognition unit 454 according to modification 8 exists in the control unit 160.

An operation according to this modification will be explained with reference to FIG. 18. FIG. 18 is a flowchart showing the operation of the imaging control apparatus 400 according to this modification. The operation in FIG. 18 is different from that in FIG. 17 explained in modification 8 in that the object recognition unit 161 exists in the radiation detection apparatus 100, so the imaging control apparatus 400 determines whether it has received a radiation irradiation sensing notification from the radiation detection apparatus 100 (step S1801). If the object recognition unit 161 determines that an object exists, the radiation detection apparatus 100 determines whether radiation irradiation has been sensed. If radiation irradiation has been sensed, the radiation detection apparatus 100 notifies the imaging control apparatus 400 that the radiation irradiation has been sensed. If the imaging control apparatus 400 receives the radiation irradiation sensing notification (YES in step S1801), it shifts to the image obtaining sequence (steps S907 to S909) as in FIG. 17. If the imaging control apparatus 400 does not receive the radiation irradiation sensing notification (NO in step S1801), it does nothing.

As described above, according to modification 9, when the radiation detection apparatus 100 notifies the imaging control apparatus 400 of sensing of radiation irradiation, including confirmation of the presence of an object, the imaging control apparatus 400 obtains a captured image. Even if the image quality is poor in the imaging control apparatus 400, the user can obtain and save an image in which the object exists, and avoid wasteful re-imaging.

In addition, in the imaging system according to this embodiment, imaging information is input, and selection of imaging information and imaging corresponding to the imaging information are alternately repeated. This is implemented, for example, as follows. The image display unit 430 displays an object information list in response to activation of the imaging control apparatus 400. One piece of displayed imaging information is selected in accordance with an operation input by the user to the imaging information input unit 460. The imaging information management unit 470 manages the selected imaging information as target imaging information to be associated with captured image data to be received next. More specifically, control is performed to store the imaging information in the memory together with supplementary information representing that this imaging information is target imaging information to be associated with captured image data to be received next. When imaging information is selected again, imaging information supplementary to the imaging information before reselection is deleted, and supplementary information representing that this imaging information is target imaging information to be associated with captured image data to be received next is associated with the imaging information after reselection, and stored in the memory. Thereafter, the irradiation switch is pressed, radiation is generated, and the communication unit 410 receives image data obtained by the radiation detection apparatus. The imaging information management unit 470 associates this image data with the imaging information to which the above-mentioned supplementary information is supplementary. The image data is then stored in the image save unit 440. In this way, imaging of one unit is completed. Upon completion of imaging, the next imaging information is selected, and the next radiation irradiation is performed. Note that the radiation detector 110 of the radiation detection apparatus 100 transits to the imaging possible state in accordance with selection of imaging information, and a normal imaging period starts.

As described above, if radiation irradiation in the normal imaging period is performed, imaging information is complete at the timing of radiation irradiation, and an image is transmitted to the imaging control apparatus 400 immediately after imaging. However, if irradiation with radiation is performed at a timing not in the normal imaging period, that is, mis-exposure is performed, imaging information to be associated does not exist. In such a case, the communication unit 410 receives an image only when imaging information is complete in the above-described embodiment. The possibility that imaging information and image data may not properly correspond to each other can therefore be reduced.

Second Embodiment

Next, an imaging system will be examined, in which when imaging is performed despite mis-exposure, the user is quickly notified of the mis-exposure to stop irradiation by the radiation generating apparatus, and a notification to request re-imaging, and the like are performed. In this case, at the time of notifying the user of mis-exposure upon detecting it, the user may not be notified of the mis-exposure if a display for presenting the notification to the user is OFF, if the user has not performed an operation for a while and the screen saver function operates, or if the user logged out. When the imaging system is operated in this state, irradiation with radiation becomes possible without any limitation in a state in which the user cannot recognize the radiation irradiation at all, so the risk of the system becomes very high. Especially at the medical site, it is often the case that the display is turned off or the screen saver function is frequently used, in order to prevent a third party from seeing patient information and imaging information. This embodiment has a feature in which the user is prompted to recognize mis-exposure by stopping the screen saver function immediately upon detecting mis-exposure.

Figure 19:
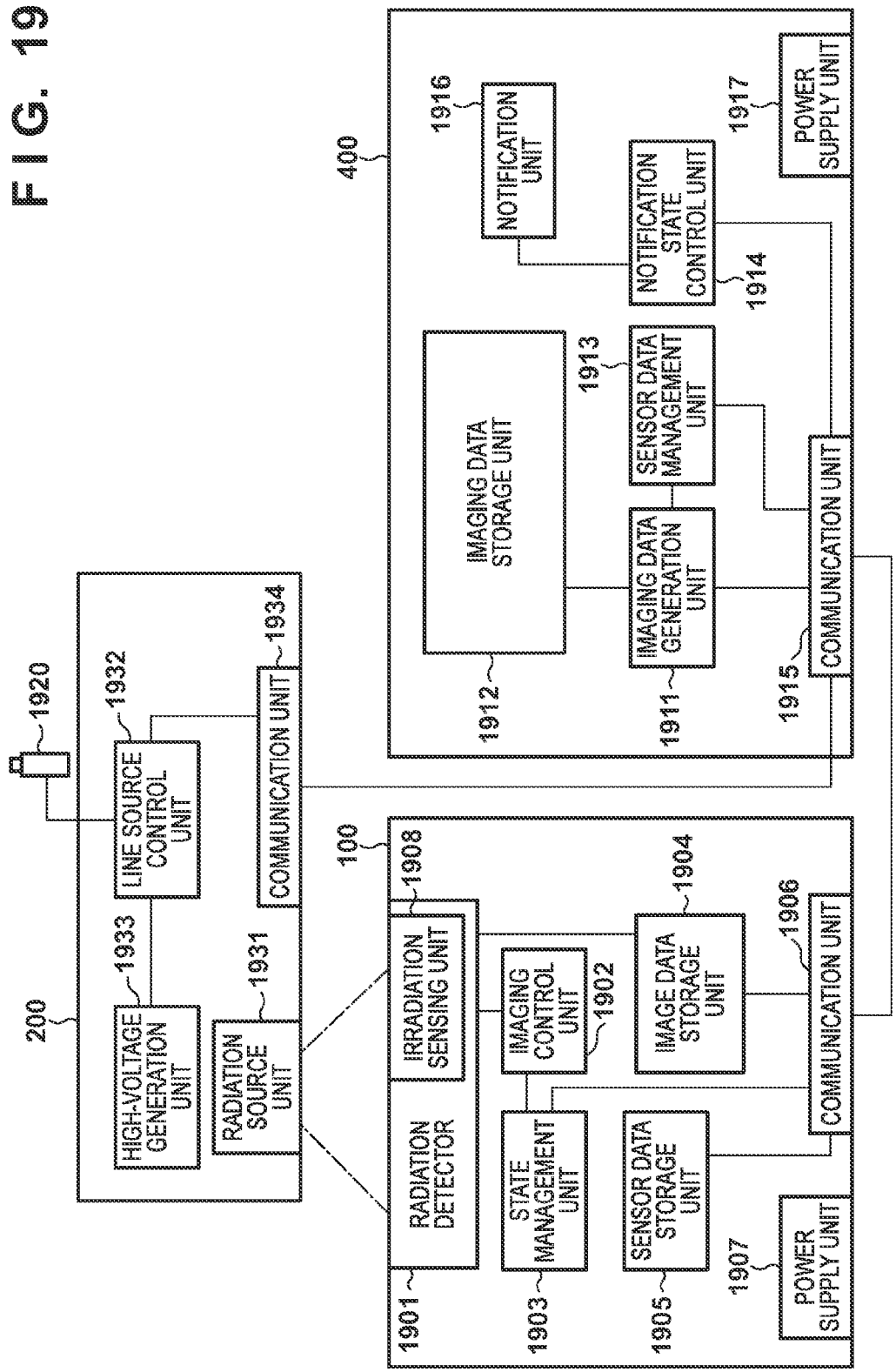
FIG. 19 is a block diagram showing the arrangement of an imaging system according to the second embodiment.
Figure 20:
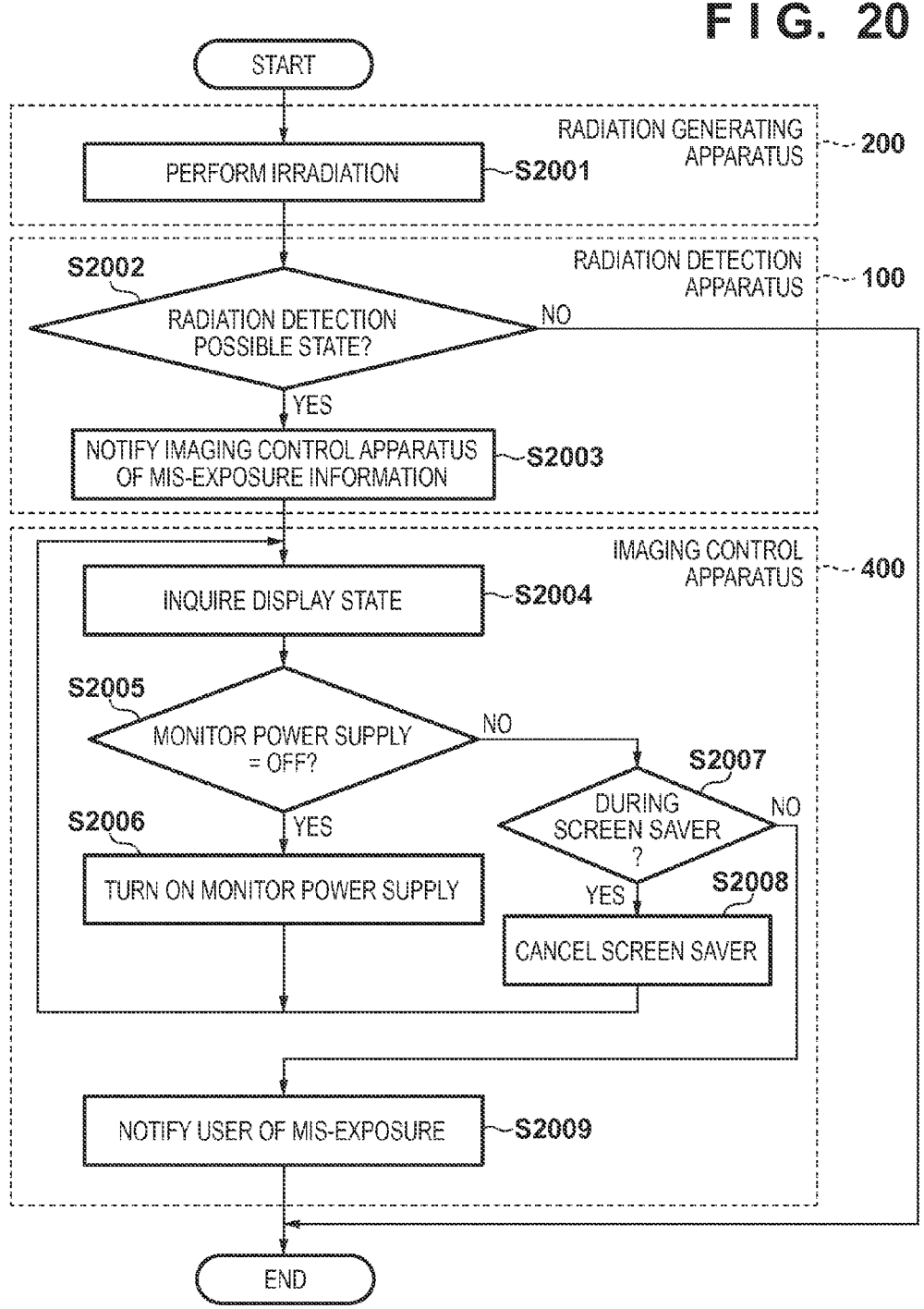
FIG. 20 is a flowchart showing the operation of the imaging system according to the second embodiment.

FIG. 19 is a block diagram showing the imaging system according to this embodiment. FIG. 20 is a flowchart showing the operation of an imaging control apparatus 400 according to this embodiment. The arrangement of the imaging system according to this embodiment will be explained first with reference to FIG. 19. Subsequently, the sequence of processing in the imaging system according to this embodiment will be explained with reference to FIG. 20.

A radiation detection apparatus 100 according to this embodiment converts radiation energy emitted by a radiation generating apparatus 200 into an electric signal, builds a digital radiation image, and transfers the image to the imaging control apparatus 400. The radiation detection apparatus 100 includes a radiation detector 1901, an imaging control unit 1902, a state management unit 1903, an image data storage unit 1904, a data storage unit 1905, a communication unit 1906, a power supply unit 1907, and an irradiation sensing unit 1908.

The radiation detector 1901 converts radiation energy received from the radiation generating apparatus 200 into a charge amount, and the charges are accumulated in the capacitors of pixels arranged in a matrix. The accumulated charges are A/D-converted via TFT (Thin Film Transistor) switches and charge amplifiers, and read out as digital values. The TFT is a transistor on a thin film and is a semiconductor element for performing a switching operation. The TFT switches are switched between ON and OFF for each row to perform scanning and read the pixels of the entire screen, thereby obtaining a radiation image.

In the radiation detector 1901, the irradiation sensing unit 1908 constituted by a plurality of photomultipliers sensitive to radiation is arranged on the back side of a sensor array. The radiation detector 1901 senses the start of irradiation or the end of irradiation based on a signal from each photomultiplier. In response to this, the radiation detector 1901 starts and ends reading of charges, and automatically senses irradiation with radiation from the radiation generating apparatus 200 and the end of the irradiation.

The imaging control unit 1902 is a building component corresponding to the control unit 160 in FIG. 1. The imaging control unit 1902 is constituted by a multiprocessor unit, and appropriately controls the radiation detector 1901 in accordance with the state of the radiation detection apparatus 100 that is managed by the state management unit 1903. For example, when the radiation detection apparatus 100 is in the standby state, the radiation detector 1901 is controlled to perform idling driving for removing charges accumulated in the capacitor of the radiation detector 1901 and reading pixel information. When the radiation detection apparatus 100 is in the ongoing imaging state, the radiation detector 1901 is controlled to perform reading driving for accumulating charges for a predetermined time, energizing the charge amplifier, and then reading image information. Assume that these driving methods are set in advance as driving programs in the multiprocessor unit. The state management unit 1903 is also constituted by a multiprocessor unit, and manages the state of the radiation detection apparatus 100.

The state of the radiation detection apparatus 100 transits in accordance with a control signal received from the imaging control apparatus 400 or the radiation generating apparatus 200. States according to this embodiment are classified into four states: an imaging possible state, ongoing imaging state, standby state, and radiation detection possible state. The communication unit 1906 receives a control signal from the imaging control apparatus 400 or the radiation generating apparatus 200, compares the signal with the current driving state of the radiation detector 1901, and when driving needs to be switched, transmits a signal designating switching of driving to the imaging control unit 1902. The radiation detection possible state indicates a state in which imaging is impossible, but when the radiation generating apparatus 200 performs irradiation with radiation, the irradiation with radiation can be detected. When the radiation detection apparatus 100 detects the radiation irradiation in this state, it determines that mis-exposure has been performed, and transmits mis-exposure information to the imaging control apparatus 400 via the communication unit 1906.

The image data storage unit 1904 is a storage area for temporarily storing image data generated by the radiation detector 1901. In general, the image data storage unit 1904 is constituted by a semiconductor storage device such as a ROM or flash memory. The image data storage unit 1904 has a minimum storage capacity for data of one image, and can have even a capacity for data of a plurality of images depending on the operation method. If image transfer from the radiation detection apparatus 100 to the imaging control apparatus 400 fails, image data is held in this storage area.

The sensor data storage unit 1905 is a storage area formed from a semiconductor storage device, and holds sensor-specific data. Main data are the serial number of a sensor, the manufacturing number, communication information such as an IP address necessary for communication with an external device, and the like. When notifying the imaging control apparatus 400 or the like of sensor information, data in the sensor data storage unit 1905 is transmitted outside.

The communication unit 1906 has a function of transferring outside image data generated by the radiation detector 1901, or sensor information held by the sensor data storage unit 1905. When the communication unit 1906 communicates with the imaging control apparatus 400 by using the TCP/IP protocol and Ethernet®, the IP address and port number of the sensor are set prior to the start of communication. A communication unit 1915 of the imaging control apparatus 400 is similarly set. Then, communication using these pieces of information is established. The communication unit 1906 does not determine whether to transfer image data. If the communication unit 1906 receives an image transfer start signal from the communication unit 1915 of the imaging control apparatus 400, it transmits image data present in the image data storage unit 1904. When there is no image data to be held in the image data storage unit 1904, and the communication unit 1906 receives an image transfer start signal, the communication unit 1906 sends back an error signal. The power supply unit 1907 is constituted by a battery or the like, and supplies power for normally operating the radiation detection apparatus 100.

The imaging control apparatus 400 according to this embodiment performs control including management of sensor information, reception of image data generated by the radiation detection apparatus 100, display of the image data on a monitor or the like, and presentation of a captured image to the user. The imaging control apparatus 400 includes an imaging data generation unit 1911, an imaging data storage unit 1912, a sensor data management unit 1913, a notification state control unit 1914, the communication unit 1915, a notification unit 1916, and a power supply unit 1917. The imaging control apparatus 400 is generally constituted by a desktop, notebook, or tablet computer. The imaging control apparatus 400 includes data input devices such as a mouse and keyboard.

The imaging data generation unit 1911 links patient information and imaging information set by the user prior to imaging with image data received by the communication unit 1915, thereby generating imaging data to be finally output. The generated imaging data is transferred to the imaging data storage unit 1912 and saved. The generated imaging data is transferred to a monitor connected to the imaging control apparatus 400 or the like, and the user can confirm the captured image.

The imaging data storage unit 1912 is constituted by a solid-state drive (SSD) for a magnetic storage device such as a hard disk or a large-capacity storage device using a semiconductor memory. The imaging data storage unit 1912 saves imaging data generated by the imaging data generation unit 1911. As another operation method, the imaging data generation unit 1911 can also transfer generated imaging data to an external storage device such as PACS (Picture Archiving and Communication System).

The sensor data management unit 1913 includes memory such as a magnetic storage device or a semiconductor memory device, and manages sensor information used in the imaging control apparatus 400. The sensor data management unit 1913 obtains sensor information held by the sensor data storage unit 1905, and manages it as a data table. At the time of imaging, when the user designates a sensor to be used, the sensor data management unit 1913 obtains sensor information from a memory incorporated in the sensor data management unit 1913, and links it with imaging data.

The notification state control unit 1914 always monitors and manages the current state of the notification unit 1916. When the radiation detection apparatus 100 outputs a mis-exposure information notification, the notification state control unit 1914 switches the notification in accordance with the state of the notification unit 1916. The notification state control unit 1914 can also manage a plurality of notification units 1916. In this case, the notification state control unit 1914 manages the notification state of each notification unit by using a data table. Similar to the sensor data management unit 1913, the notification state control unit 1914 is constituted by a magnetic storage device or a semiconductor memory device. The notification state control unit 1914 can also be constituted by sharing the imaging data storage unit 1912 and the sensor data management unit 1913.

As a method of managing the notification state of the notification unit 1916, for example, there is a method using a command capable of transmitting/receiving a window-related notification message WM_SYSCOMMAND, which is one window message usable in the Windows® OS environment. By transmitting this command to the notification unit 1916, the notification state control unit 1914 can switch the monitor power supply, and activate utility software (to be referred to as a screen saver hereinafter) which is automatically activated to protect the monitor when there is no input operation from the user for a long time. The notification state control unit 1914 can keep transmitting this command to the notification unit 1916 at a predetermined interval and manage the display state at this time as a data table in the notification state control unit 1914.

The communication unit 1915 has the same role as that of the communication unit 1906 of the radiation detection apparatus 100. Information for establishing communication is set in advance, and the communication unit 1915 exchanges image data, sensor information, and the like. The notification unit 1916 notifies the user that mis-exposure has been detected. The method of this notification is not limited to one and includes emission of light and output of a sound. The imaging control apparatus 400 can also adopt a method of displaying a message on a monitor connected to the imaging control apparatus 400 or the like, or outputting a notification using an external device. For example, when the imaging control apparatus 400 is connected to an LED emission device or the like, it is conceivable that the user is notified of mis-exposure by transmitting a communication command which causes the emission device to emit light and the imaging control apparatus 400 to output a sound upon detecting mis-exposure. The power supply unit 1917 supplies power to the entire imaging control apparatus 400.

The radiation generating apparatus 200 performs irradiation with radiation by applying a high voltage generated from a high-voltage generation unit 1933 to a radiation source unit 1931 in accordance with irradiation conditions such as the tube current and radiation duration, which are set by the user prior to imaging. The radiation generating apparatus 200 includes the radiation source unit 1931, a line source control unit 1932, the high-voltage generation unit 1933, and a communication unit 1934. Irradiation with radiation from the radiation generating apparatus 200 is performed when the user presses an irradiation switch 1920, and ends when the user releases the switch.

Next, the sequence of processing in the imaging system according to this embodiment will be explained with reference to FIG. 20. First, assume that the user operates the irradiation switch 1920 to perform irradiation with radiation while the radiation detection apparatus 100 is not in the imaging possible state but in the radiation detection possible state (steps S2001 and S2002). Needless to say, when the radiation detection apparatus 100 is in the standby state in which detection of irradiation with radiation is impossible, it cannot detect radiation irradiation. If the radiation detection apparatus 100 is in the imaging possible state, a radiation image is generated by the radiation detector 1901 and saved in the image data storage unit 1904.

In the radiation detection apparatus 100, the radiation detector 1901 notifies the state management unit 1903 that the radiation irradiation has been detected. If the radiation detection apparatus 100 is not in the imaging possible state but in the radiation detection possible state, the state management unit 1903 transmits mis-exposure detection information to the imaging control apparatus 400 (step S2003). In the imaging control apparatus 400, the notification state control unit 1914 is notified of the mis-exposure information via the communication unit 1915. The notification state control unit 1914 inquires regarding a display state of the notification unit 1916 (step S2004). If the monitor power supply is OFF (YES in step S2005), the notification unit 1916 sends back, to the notification state control unit 1914 in response to the inquiry, a signal representing that the monitor power supply is OFF. In this case, the notification state control unit 1914 transmits, to the notification unit 1916, a signal for turning on the monitor power supply (step S2006). If the monitor power supply is ON (NO in step S2005) and the screen saver is being displayed (YES in step S2007), the notification unit 1916 sends back, to the notification state control unit 1914, a signal representing that the screen saver is being displayed. In this case, the notification state control unit 1914 transmits, to the notification unit 1916, a signal for canceling the screen saver function (step S2008). The inquiry (step S2004) is repeated until the notification unit 1916 becomes able to normally notify the user of mis-exposure information.

If the notification unit 1916 changes to the normal notification possible state, the notification state control unit 1914 transmits mis-exposure information to the notification unit 1916 (step S2009). The notification unit 1916 performs processing of notifying the user of the received mis-exposure information. The method of notifying the user of the mis-exposure information is not limited to a specific method, as described above. Note that when a message or the like is displayed on the monitor and another window or dialog is being displayed, the mis-exposure information is processed to display it on the foreground with respect to other display items, thereby preventing a state in which the user cannot confirm the mis-exposure information. For this purpose, the notification state control unit 1914 obtains information of a window or dialog during display on the monitor and performs control to output the mis-exposure information notification on the foreground.

As described above, according to the second embodiment, even when the notification state control unit 1914 detects mis-exposure information in a state in which the notification unit 1916 cannot quickly output a mis-exposure notification, it is controlled to automatically output the mis-exposure notification without requiring an operation by the user. This can prevent leaving the user in a state in which he cannot recognize mis-exposure at all.

[Modification]

The second embodiment has described a method of notifying the user of mis-exposure in a state in which, for example, the screen saver is being displayed and an information notification to the user cannot be displayed quickly. This modification will describe a form in which a user notification upon detecting mis-exposure is performed immediately when a state in which an operation (to be referred to as log-in hereinafter) of identifying the identity and validity of a user and obtaining necessary qualification information at the start of using the operation system (to be referred to as an OS hereinafter) of the control apparatus changes to a state in which the session is ended (to be referred to as log-out hereinafter).

Figure 21:
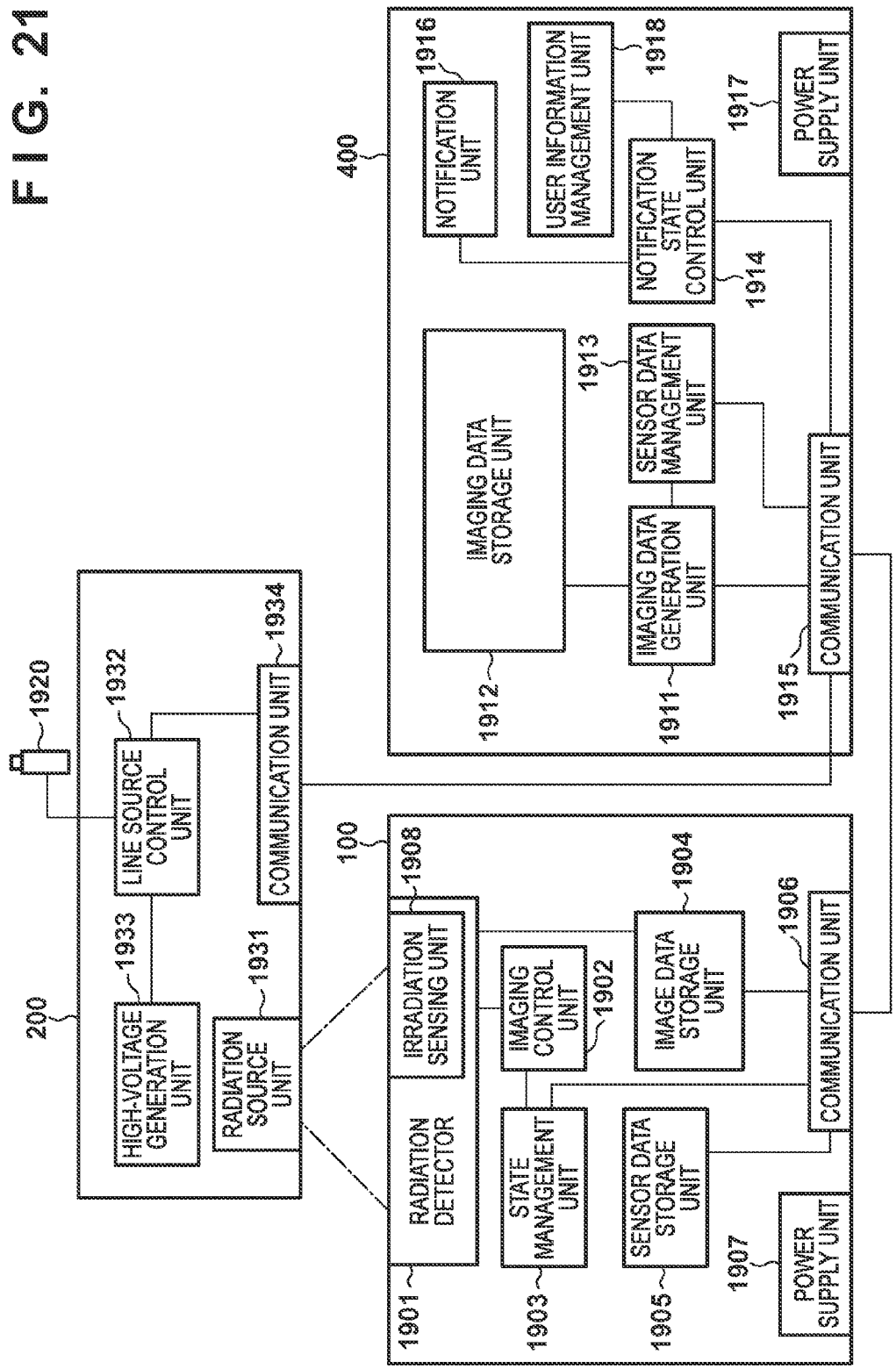
FIG. 21 is a block diagram showing the arrangement of the imaging system according to a modification of the second embodiment.
Figure 22:
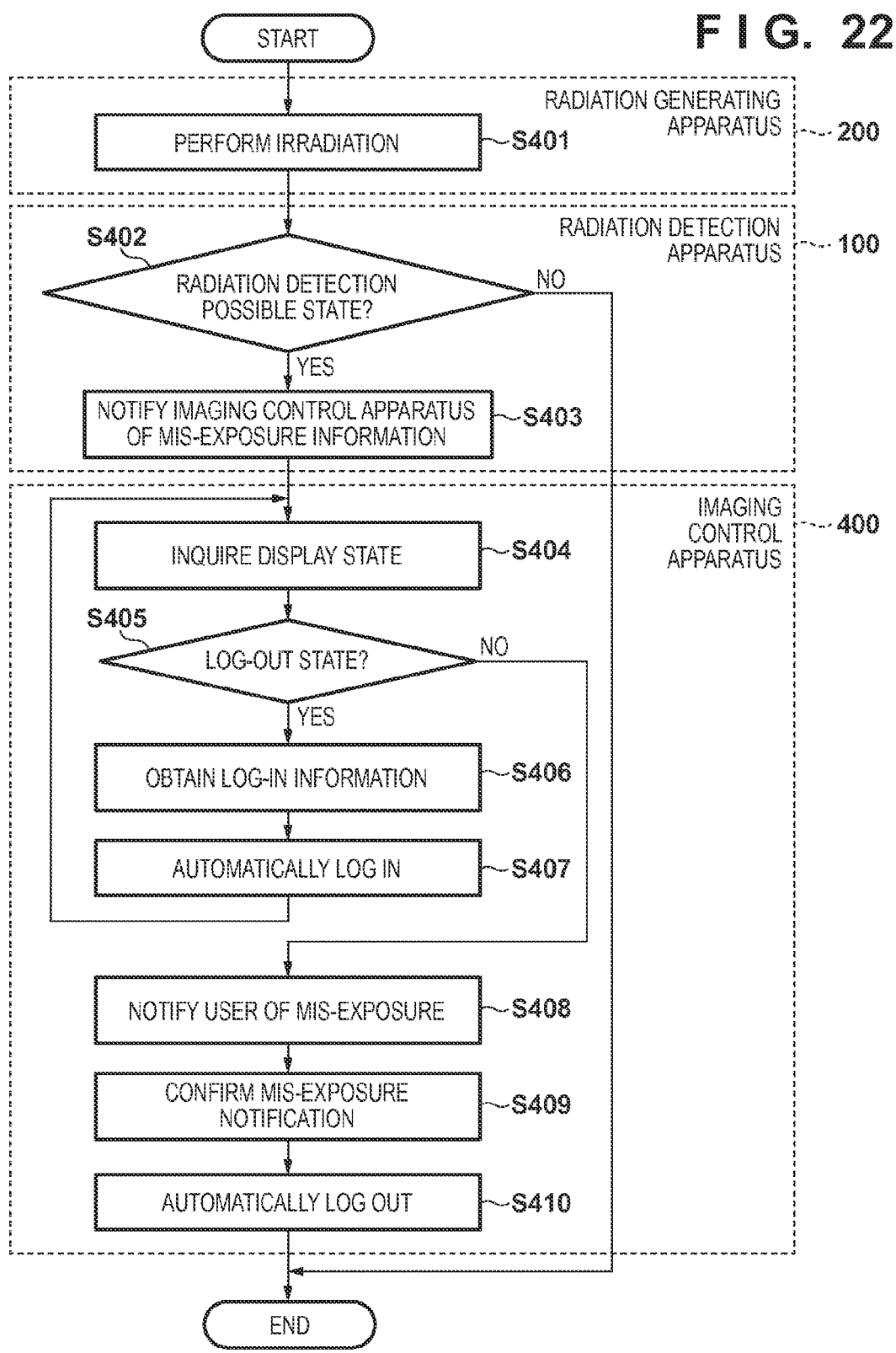
FIG. 22 is a flowchart showing the operation of the imaging system according to the modification of the second embodiment.

FIG. 21 is a block diagram showing the arrangement of the imaging system according to this modification. FIG. 22 is a flowchart showing the operation of the imaging system according to this modification. The arrangement of the imaging system according to this modification will be explained first with reference to FIG. 21. Subsequently, the sequence of processing in the imaging control apparatus 400 according to this modification will be explained with reference to FIG. 22.

In the imaging control apparatus 400 according to this modification, a user information management unit 1918 is constituted by a magnetic storage device or a semiconductor memory device, and obtains and manages the latest OS log-in information. The user information management unit 1918 manages user information in a data table, and manages operation authority permitted for each user. For example, the imaging control apparatus 400 can make a setting to limit, to restrictive users, users who can change the basic settings of the system and the like, and inhibit a change by general users.

Next, the sequence of processing in the imaging system according to this modification will be explained with reference to FIG. 22. As in the second embodiment, if irradiation with radiation is performed when the radiation detection apparatus 100 is in the radiation detection possible state (steps S401 and S402), the radiation detector 1901 notifies the state management unit 1903 that the radiation irradiation has been detected. The state management unit 1903 determines that this radiation irradiation is mis-exposure, and notifies the notification state control unit 1914 via the communication unit 1906 of the mis-exposure information (step S403).

In the imaging control apparatus 400, upon receiving the mis-exposure information, the notification state control unit 1914 inquires regarding a notification state of the notification unit 1916 (step S404). If the notification unit 1916 sends back a signal representing the log-out state, the notification state control unit 1914 requests the user information management unit 1918 to obtain user information necessary for log-in (step S406). The user information management unit 1918 sets in advance user information at the time of a mis-exposure notification, and notifies the notification state control unit 1914 of the user information. By using this user information, the notification state control unit 1914 performs log-in processing (step S407). After confirming a state in which the user can be normally notified of mis-exposure information, the notification state control unit 1914 performs a mis-exposure notification via the notification unit 1916 (step S408). The notification method is not limited to one, as in the first embodiment.

At this time, assume that the user can set in advance user information to be temporarily used, in order to notify the user of mis-exposure information. Basically, because of a log-in operation only for notifying the user of information, special log-in information incapable of all imaging operations and setting changes is desirably set. User information having imaging authority can also be set so that imaging can be started immediately after detecting mis-exposure, in order to put importance on user operability though security becomes poor.

The user confirms the mis-exposure information via the notification unit 1916 (step S409). For example, when the mis-exposure information is displayed on a monitor or the like, for example, the user clicks a confirmation button using an I/O interface such as a mouse to notify the imaging control apparatus 400 that he has confirmed the mis-exposure information. When the user is notified of mis-exposure information by light of an LED lamp or the like, for example, the user presses the switch of the lamp to notify the imaging control apparatus 400 that he has confirmed the mis-exposure information. Upon receiving the confirmation information from the user, the notification state control unit 1914 automatically performs log-out control of the OS in order to return again to the log-out state (step S410). Thus, even if processing of logging in to the OS is automatically performed for a mis-exposure notification, a user having no operation authority can be inhibited from continuing the operation.

As described above, according to this modification, even if the imaging control apparatus 400 is in the log-out state upon detecting mis-exposure by the radiation detection apparatus 100, the user can be automatically notified of mis-exposure information without paying attention to the display state. Even if the imaging control apparatus 400 temporarily changes to the log-in state, it is set in advance to minimize user authority at this time, and a malfunction by the user can also be prevented.

Each unit constituting the imaging system according to each of the above-described embodiments of the present invention, and each step of processing by the unit can be implemented when a program stored in the RAM or ROM of a computer or the like runs. The present invention incorporates the program, and a computer-readable recording medium on which the program is recorded.

Each of the radiation detection apparatus, radiation control apparatus, radiation detection apparatus, imaging control apparatus, and the like included in the imaging system according to each of the embodiments of the present invention may be implemented by a system constituted by a plurality of independent apparatuses. Even such an embodiment falls within the embodiments of the present invention. In this case, the independent apparatuses communicate with each other via a network or directly by peer-to-peer, and the plurality of apparatuses cooperate with each other, thereby implementing the above-described imaging system. For example, the image save unit 440 and image processing unit 420 of the imaging control apparatus 400 shown in FIG. 4 may be independent of the imaging control apparatus 400 and shared as an image management server and image processing apparatus between a plurality of imaging systems. Alternatively, the plurality of independent apparatuses described above may be arranged in different countries.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-158124, filed Aug. 1, 2014, which is hereby incorporated by reference herein in its entirety.

What is claimed is:

1. A management apparatus which manages an image captured in a radiation detection apparatus by irradiation with radiation, comprising:
   a management unit configured to manage imaging information which is input by a user and serves as information for imaging;
   an obtaining unit configured to obtain the captured image; and
   an association unit configured to associate the obtained image with the imaging information,
   wherein when a mis-exposure notification is received from the radiation detection apparatus and said management unit manages necessary imaging information, said obtaining unit obtains the captured image.

2. The apparatus according to claim 1, further comprising a notification unit configured to, when the mis-exposure notification is received from the radiation detection apparatus and said management unit does not manage the necessary imaging information, notify a user to prompt input of the necessary imaging information.

3. The apparatus according to claim 1, wherein when the mis-exposure notification is received from the radiation detection apparatus and said management unit does not manage the necessary imaging information, said obtaining unit does not obtain the captured image.

4. The apparatus according to claim 1, further comprising a save unit configured to save the image associated with the imaging information by said association unit.

5. The apparatus according to claim 1, further comprising a display unit configured to display, on the display, the image associated with the imaging information by said association unit.

6. A management apparatus which manages an image captured in a radiation detection apparatus by irradiation with radiation, comprising:
   a management unit configured to manage imaging information which is input by a user and serves as information for imaging;
   an obtaining unit configured to obtain the captured image;
   an identification unit configured to identify an image not obtained by said obtaining unit out of images captured in the radiation detection apparatus; and
   an association unit configured to associate the obtained image with the imaging information,
   wherein said obtaining unit obtains an unobtained image identified by said identification unit.

7. The apparatus according to claim 6, wherein said identification unit identifies an image not obtained by said obtaining unit when a connection between the radiation detection apparatus and the management apparatus is established.

8. The apparatus according to claim 6, wherein said identification unit identifies an image not obtained by said obtaining unit, based on information for identifying an image received from the radiation detection apparatus.

9. A management apparatus which manages an image captured in a radiation detection apparatus by irradiation with radiation, comprising:
   a management unit configured to manage imaging information which is input by a user and serves as information for imaging;
   an obtaining unit configured to obtain the captured image;
   a determination unit configured to determine whether a predetermined elapsed time has elapsed after the radiation detection apparatus starts an initializing operation for removing charges generated by a dark current generated in a photoelectric conversion element and by radiation irradiation; and
   an association unit configured to associate the obtained image with the imaging information,
   wherein when a mis-exposure notification is received from the radiation detection apparatus and said determination unit determines that the elapsed time has elapsed, said obtaining unit obtains the captured image.

10. The apparatus according to claim 9, wherein the elapsed time is set to be a time longer than a time necessary to obtain an image higher in image quality than a predetermined level by said obtaining unit.

11. The apparatus according to claim 9, wherein when an intention to obtain an image is confirmed by the user, said obtaining unit obtains the captured image.

12. The apparatus according to claim 9, wherein when said determination unit does not determine that the elapsed time has elapsed, said obtaining unit obtains the captured image, and obtains the image as a rejected image.

13. A management apparatus which manages an image captured in a radiation detection apparatus by irradiation with radiation, comprising:
   a management unit configured to manage imaging information which is input by a user and serves as information for imaging;
   an obtaining unit configured to obtain the captured image;
   a determination unit configured to determine whether an object exists in the captured image; and
   an association unit configured to associate the obtained image with the imaging information,
   wherein when a mis-exposure notification is received from the radiation detection apparatus and said determination unit determines that the object exists in the image, said obtaining unit obtains the captured image.

14. The apparatus according to claim 13, wherein, by extracting one of a histogram and edge of the captured image, said determination unit determines whether the object exists.

15. The apparatus according to claim 13, wherein, based on information received from the radiation detection apparatus, said determination unit determines whether the object exists in the captured image.

16. The apparatus according to claim 15, wherein the information received from the radiation detection apparatus is information representing whether the object exists, which is determined by extracting one of a histogram and edge of the captured image by the radiation detection apparatus.

17. The apparatus according to claim 15, wherein when sensing of radiation irradiation is received from the radiation detection apparatus, said obtaining unit obtains the captured image.

18. A management apparatus which includes a display configured to display a patient information input/examination selection screen and an imaging screen, and manages an image captured in a radiation detection apparatus by irradiation with radiation, comprising:
   a control unit configured to control display by the display;
   a management unit configured to manage imaging information which is input from a user to display of the patient information input/examination selection screen on the display;

an obtaining unit configured to obtain the captured image; and an association unit configured to associate the obtained image with the imaging information, wherein said control unit displays the imaging screen after the imaging information is input, and when a mis-exposure notification is received from the radiation detection apparatus and the display displays the imaging screen, said obtaining unit obtains the captured image.

19. A management apparatus which manages an image captured in a radiation detection apparatus by irradiation with radiation, comprising:

a notification unit configured to notify a user that a mis-exposure notification has been received from the radiation detection apparatus; and a control unit configured to control a state of said notification unit, wherein when the state of said notification unit is a state in which a notification to the user cannot be performed, said control unit changes the state of said notification unit so as to perform the notification.

20. The apparatus according to claim 19, wherein when said notification unit is in a state in which a notification cannot be performed because a screen saver is displayed, said control unit cancels a function of the screen saver and changes the state to a state in which said notification unit can perform the notification.

21. The apparatus according to claim 19, wherein when said notification unit is in a state in which a notification cannot be performed because a power supply is OFF, said control unit turns on the power supply and changes said notification unit to a state in which said notification unit can perform the notification.

22. The apparatus according to claim 19, wherein when said notification unit is in a state in which a notification cannot be performed because of a log-out state, said control unit performs log-in processing using necessary user information and changes said notification unit to a state in which said notification unit can perform the notification.

23. The apparatus according to claim 22, wherein the user information can be arbitrarily set by the user.

24. The apparatus according to claim 19, wherein said control unit returns the state of said notification unit to an original state in response to confirmation, by the user, of the notification by said notification unit.

\* \* \* \* \*